(12) United States Patent
Yadav

(10) Patent No.: US 7,115,798 B1
(45) Date of Patent: Oct. 3, 2006

(54) METHODS FOR REGULATED EXPRESSION OF TRIATS IN PLANTS USING MULTIPLE SITE-SPECIFIC RECOMBINATION SYSTEMS

(75) Inventor: Narendra S Yadav, Chadds Ford, PA (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 09/715,294

(22) Filed: Nov. 17, 2000

Related U.S. Application Data

(63) Continuation-in-part of application No. 09/442,021, filed on Nov. 17, 1999, now Pat. No. 6,632,980.

(51) Int. Cl.
*C12N 15/82* (2006.01)
*C12N 15/87* (2006.01)
*C12N 15/90* (2006.01)

(52) U.S. Cl. ...................................... 800/278; 800/287

(58) Field of Classification Search ............. 435/320.1, 435/410, 419, 468; 800/278, 410, 419, 468, 800/287
See application file for complete search history.

(56) References Cited

U.S. PATENT DOCUMENTS

| | | | |
|---|---|---|---|
| 5,658,772 A | 8/1997 | Odell et al. ................. | 435/419 |
| 5,723,765 A | 3/1998 | Oliver et al. ................ | 800/278 |
| 5,910,415 A | 6/1999 | Hodges et al. ................. | 435/6 |
| 5,925,808 A | 7/1999 | Oliver et al. ............... | 800/298 |
| 5,929,307 A | 7/1999 | Hodges et al. .............. | 800/303 |
| 5,965,791 A | 10/1999 | Ebinuma et al. ............ | 800/278 |
| 5,977,441 A | 11/1999 | Oliver et al. ............... | 800/298 |
| 6,110,736 A | 8/2000 | Hodges et al. ........... | 435/320.1 |
| 2002/0147168 A1* | 10/2002 | Surin et al. | |

FOREIGN PATENT DOCUMENTS

| | | |
|---|---|---|
| WO | WO/91099 57 | 7/1991 |
| WO | WO 9109957 | 7/1991 |
| WO | WO 93/01283 A1 | 1/1993 |
| WO | WO/94036 19 | 2/1994 |
| WO | WO 96 04393 A | 2/1996 |
| WO | WO 9706269 A1 | 2/1997 |
| WO | WO 9711189 A2 | 3/1997 |
| WO | WO 97/37012 A1 | 10/1997 |
| WO | WO 9838323 A2 | 9/1998 |
| WO | WO/99118 07 | 3/1999 |
| WO | WO/99258 40 | 5/1999 |
| WO | WO/99258 41 | 5/1999 |
| WO | WO/99258 54 | 5/1999 |
| WO | WO 00 17365 | 3/2000 |
| WO | WO 00/60091 | 10/2000 |

OTHER PUBLICATIONS

Odell et al, "Site-directed recombination in the genome of transgenic tobacco". 1990. Mol Gen Genet vol. 223, pp. 369-378.*
Lloyd et al. "Functional expression of the yeast FLP/FRT site specific recombination system in *Nictiana tabacum*", 1994. Mol Gen Genet vol. 242, pp. 653-657.*
Odell et al., Use of site-specific recombination systems in plants. Homologous Recomb. Gene Silencing Plants (1994), 219-70, Editors: Paszkowski, Jerzy, Publisher: Kluwer, Dordrecht, Germany.
Zubko et al., (2000) Nature Biotechnology 18:442.
Groth et al., (2000) Proc. Natl. Acad. Sci. USA 97:5995.
H Matsuzaki et al., J Hbacteriology, vol. 172, p. 610, 1990.
H. Onouchi et al., Nucleic Acid Res., vol. 19, p. 6373, 1991.
Mariani et al., Induction of Male Sterility in Plants by a Chimaeric Ribonuclease Gene, Nature GB MacMillan Journals LTD. London, vol. 347, Oct. 25, 1990 pp. 737-741.
Lyznik et al , FLP-mediated recombination of FRT sites in the maize genome Nucleic Acids Research, 1996, vol. 24, No. 19, pp. 3784-3789.
Kilby et al., FLP recombinase in transgenic plants: Constitutive activity in stably transformed tobacco and generation of marked cells clones in *Arabidopsis*, Plant Journal, 1995, vol. 8, No. 5, pp. 637-652.
Odell et al., Site-directed Recombination in the Genome of Transgenic Tobacco. Mol. Gen. Genet. 1990 223 (3), 369-378.
McGonigle, Brian et al., "Nuclear localization of the *Arabidopsis* APETALA3 and PISTILLATA homeotic gene products depends on their simultaneous expression," Genes & Development. vol. 10, No. 14, 1996, pp. 1812-1821, XP000996028.
Theerakulpisut, P. et al., "Isolation and Developmental Expression of BCP1 and Anther-Specific CDNA Clone in *Brassica-campestris*" Plant Cell, vol. 3, No. 10, 1991, pp. 1073-1084, XP000986143.
De Veyloer, L. et al., Plant Cell Physiol. 38:568-577 (1997).

(Continued)

*Primary Examiner*—Ashwin Mehta

(57) ABSTRACT

This invention relates to constructs for the conditional or regulated expression of transgenes in plants using site-specific recombinase systems. The constructs comprise a variety of constitutive, inducible, tissue specific or developmental stage-specific promoters operably linked to either a transgene or the elements of one or more site-specific recombinase system. By matching promoters, responsive to various inducers, plant tissues or plant developmental states with the recombinase systems, stop fragments and transgenes, virtually any trait may be expressed at any plant development stage or in any plant generation.

7 Claims, 8 Drawing Sheets

OTHER PUBLICATIONS

Gatz, C., Annu. Rev. Plant Physiol. Plant Mol. Biol. 48:89-108 (1997).
Hansen, G. et al., Mol. Gen. Genet. 254:337-343 (1997).
Odell, J. T. et al., Plant Physiol. 106:447-458 (1994).
van der Geest et al., Plant Physiol., 109(4), 1151-58 (1995).
Ma et al., Aust. J. Plant. Physiol., 25(1), 53-59 (1998).
Czako et al., Mol. Gen. Genet., 235(1), 33-40 (1992).
Albert et al., Plant J. 7:649-59(1995).
Araki et al., Nucleic Acids Res. 25:868-872 (1997).
Russell et al., Mol. Gen. Genet. 234:49-59 (1992).
N.L. Craig, Annu Rev Genet., vol. 22, p. 77-105, 1988.
David W. Ow. The Right Chemistry for Marker Gene Removal, Nature Biotechnology. vol. 19. Feb. 2001, pp. 115/116.

* cited by examiner

Stage 1: R1 recombinase expression occurs under promoter (P1) primes trait gene (TG)

Stage 2: TG expression occurs under P2 promoter, e.g. mature leaf promoter

Stage 1: Trait expression occurs under promoter P2

Stage 2: R1 recombinase expression occurs under male or floral common germline promoter (P1) removes trait gene from pollen or progeny seed of first generation, respectively.

Stage 1: R1 recombinase expression occurs under common germline promoter (P1) primes R2 gene.

Stage 2: R2 recombinase expression occurs under floral common germline promoter (P2) primes trait gene TG.

Stage 3: TG expression occurs under promoter P3, e.g., embryo or germination promoter

METHODS FOR REGULATED EXPRESSION OF TRIATS IN PLANTS USING MULTIPLE SITE-SPECIFIC RECOMBINATION SYSTEMS

This application is a continuation in part of U.S. Ser. No. 09/442,021, filed Nov. 17, 1999, now U.S. Pat. No. 6,632,980.

FIELD OF INVENTION

The present invention relates to the field of molecular biology and the genetic transformation of plants with foreign gene fragments. More particularly, the invention relates to methods for the conditional or regulated expression or excision of genetic traits from plant progeny using site specific recombinase constructs.

BACKGROUND OF THE INVENTION

The advent of genetically modified crops holds the promise of improving crop yield and productivity as well as reducing the number of pesticides and other toxic compounds needed for crop success. These benefits are conferred via the transformation of crop plants with new genes beneficial to growth or conveying disease or pathogen resistance. However, transformation events often result in the presence of ancillary genetic material that is not useful for the expression of the desired trait. These ancillary sequences are necessary for the transformation processes, but they do not positively contribute to the final cultivar and in fact lessen its desirability to the consumer. The presence of these undesirable sequences may also complicate the regulatory procedures necessary to bring the cultivar to the market place. A reliable method for eliminating the unwanted ancillary sequences would thus improve commercial viability by increasing public acceptance and simplify the regulatory process. Additionally, it will be useful to have certain traits only present during intermediate generations and then removed in harvested generations. The prior art has not recognized the importance of these problems, nor has it worked to provide a solution.

Plants are increasingly being looked to as platforms for the production of materials, foreign to plant systems. As the art of genetic engineering advances it will be possible to engineer plants for the production of a multiplicity of monomers and polymers, currently only available by chemical synthetic means. The accumulation of these materials in various plant tissues will be toxic at some level and it will be useful to tightly regulate the relevant genes to prevent expression in inappropriate plant tissues.

Currently few methods exist that provide for tightly regulated transgene expression. Non-specific expression of transgenes in non-target cells, tissues, or generation hinders plant transgenic work. This is important where the goal is to produce such high levels of materials in transgenic plants that may be phytotoxic or adversely affects normal plant development. Conditional transgene expression would enable economic production of desired chemicals, monomers, and polymers at levels likely to be phytotoxic to growing plants by restricting their production to production tissue of transgenic plants either just prior to or after harvest of the crop biomass used for extracting the desired product. Therefore, lack of a commercially usable conditional expression system and the difficulty in attaining a reliable, high-level expression both limit development of transgene expression in plants.

Conditional or regulated expression has been reported in plants (see De Veylder, L. et al., *Plant Cell Physiol.* 38:568–577 (1997); Gatz, C., *Annu. Rev. Plant Physiol. Plant Mol. Biol.* 48:89–108 (1997); Hansen, G. et al., *Mol. Gen. Genet.* 254:337–343 (1997); Jepson, I., PCT Int. Appl. WO 9706269 A1 (1997), Jepson, I, et al. PCT Int. Appl. WO 9711189 A2 (1997), and other references within this application). However, when tested stringently for basal non-specific expression, very few have been strictly specific (Odell J. T. et al., *Plant Physiol.* 106:447–458 (1994); van der Geest et al., *Plant Physiol.,* 109(4), 1151–58 (1995); Ma et al., *Aust. J. Plant Physiol.,* 25(1), 53–59 (1998); Czako et al., *Mol. Gen. Genet.,* 235(1), 33–40 (1992)). Such promoters are not suitable for some applications, such as the use of transgenes for expressing novel phytotoxic proteins, enzymes that lead to the biosynthesis of phytotoxic products, and/or gene silencing. Site-specific recombination in plants (Odell et al., *Plant Physiol.* 106:447–458 (1994); Odell et al., PCT Int. Appl. WO 9109957 (1991); Surin et al., PCT Int. Appl WO 9737012 (1997)) and the reduction in the proficiency of Cre-mediated recombination by mutant lox P sites and their use in increasing the frequency of Cre-lox based integration have been reported (Albert et al., *Plant J.* 7:649–59 (1995); Araki et al., *Nucleic Acids Res.* 25:868–872 (1997')). However, the use of the mutant sites to enhance the specificity Cre-mediated recombination in conjunction with chimeric Cre genes under the control of available regulated promoters has not been demonstrated. Thus, there is a need for an appropriately stringent, site-specific recombination system for a commercially-attractive, conditional site-specific recombination.

Directed excision of a transgene from the plant genome has been reported using recombinase specific-sites and a recombinase. In Russel et al. (*Mol. Gen. Genet.* 234:49–59 (1992)), utility of these techniques is evaluated to remove a selectable marker for transformation from the plant, while leaving a preferred non-selectable trait. Variation in efficiency of excision of transgenes in different plants was also examined and comparison was made between introduction of the cre gene by re-transformation or by cross pollination. However, incorporation of promoters for conditional or regulated expression was not attempted.

Ow et al. (PCT Int. Appl. WO 9301283 A1 (1992)) also examine directed excision of selectable markers for trans-formation from plants, while leaving a preferred non-selectable trait that could be operably linked to control sequences capable of effecting the timing of said expression in higher plants. Their disclosed technique is limited by the requirement that the recombinase for excision must be introduced via a second round of transformation either directly to the initially transformed plants or by cross pollination of the independently regenerated plants from first and second round transformants.

In one disclosure, Oliver et al. (U.S. Pat. No. 5,977,441) demonstrate limited expression of a desired introduced gene in a transgenic plant, according to a particular stage of plant development, a particular plant tissue, particular environmental conditions, or a particular time or location. This is achieved via: 1) the insertion of a transiently-active promoter in functional relation with a structural gene whose expression results in an altered plant phenotype, but separated by a blocking sequence that is flanked by specific excision sequences; and 2) a second DNA sequence that comprises an inducible promoter operably linked to a gene encoding a site-specific recombinase. These methods ultimately permit the expression of certain plant traits to be under external control by application of an external stimulus, through hybridization, or by direct introduction of a recombinase into a plant. However, Oliver et al. did not consider the need for eliminating unwanted ancillary sequences, such as selection markers.

Surin et al. (PCT Int. Appl. WO 9737012 A1 (1997)) disclose a method whereby single-step excision of transgenes is achieved, such as selectable marker genes or reporter genes, from genetically-transformed organisms. This is possible by the incorporation of both a recombinase genetic unit (comprising a promoter, recombinase gene, and terminator) and a transgene unit (comprising a promoter, transgene, and terminator) within a single expression cassette, all flanked by recombinase sites. This genetic unit facilitates multiple sequential genetic transformation events using the same selectable marker gene and provides means for tightly regulating transgene expression in genetically-manipulated plants. Additionally, the need for multiple transformation events or sexual crossing to produce a single cell comprising both the loci for DNA recombination and the site-specific recombinase is alleviated, since their method facilitates precise excision of genetic material in a single generation using promoters that are differentially activated. Although Surin et al. allow for the incorporation of a second separate expression cassette, their techniques are limited in that a maximum of two transgenic units may be expressed within the plant at different time periods, the first of which must be removed prior to the expression of the second. At no point may the second transgene be removed from the genome if desired.

Hodges et al. (U.S. Pat. No. 6,110,736) describe a method based on homologous recombination which enables the targeting of a length of DNA to a specific non-lethal site in the host's genome, and provides for the removal of any randomly inserted DNA sequences, using site-specific recombinase sites and the corresponding recombinase protein. The need met through the application of the site-specific recombinase system for gene excision is specifically to maintain control over the copy number and the location of the inserted DNA. A further embodiment of the invention combines use of cre/lox and FLP/FRT to ultimately leave only the desired DNA sequences integrated into the chromosome while the selectable marker is removed from the chromosome. However, this work relies is confined to instances where precise homologous recombination can be executed, which necessarily requires precise engineering of the vector sequences to match sequences within the chromosome.

Finally, Perez and Flament (PCT Int. Appl. WO 9838323 (1998)) discuss the insertion of a of a male sterility gene (AMS) to create a cytoplasmic or nuclear male sterile plant. This plant avoids the dissemination of pollen, and therefore necessarily prevents dissemination of any transgenes that are linked to the male sterility genes. In further embodiments of their invention, the AMS gene can serve as a positive marker for the screening of plants having integrated a transgene of interest; or, the gene, when genetically linked to a transgene, can be excised using a system of transposition (e.g. systems of recombination such as Cre/lox or FLP/FRT). Limitations of these techniques focus on the requirement that a transgene must be directly linked to a transgene, thereby requiring linked expression. No allowance is made for conditional expression, whereby expression of one gene may activate, or excise, another later in the life cycle.

The methods described above are useful for removal of transgenes and ancillary genetic material from plants but are limited in their ability to regulate transgene expression at various times in a plant life cycle or in hybrid progeny. The problem to be solved therefore is to develop a method for the tightly regulated conditional expression and removal of genetic traits in plants, both in initial transformants and in hybrid.

Applicant has solved the stated problem by providing developmentally regulated germ-like promoters that allow using at least two different recombinases for the selective expression and/or removal of genetic traits.

SUMMARY OF THE INVENTION

The present invention provides methods for the conditional or regulated expression of a transgene in a plant, or the excision of a trait or marker in a plant using a suite of constitutive, inducible, tissue specific or developmental stage-specific promoters in combination with at least one recombinase system. Transgenes may encode specific traits, including transformation markers. By pairing the promoters with the appropriate recombinase and/or transgenes virtually any trait may be expressed at any time during a plant life cycle. Similarly, traits whose usefulness is limited to one portion of the life cycle or to only one generation may be selectively excised from subsequent generations.

For example, it is contemplated that different site specific recombinase systems under the control of different promoters may be combined or linked to enable a series of genetic switches for the regulated expression as well as removal of transgenes staggered over time during a single life cycle of the organism. Removal of transgene(s) from transgenic crops is useful for safety and protection of the environment, enhanced breeding, or for conditional transgene expression in only one generation, such as male sterility. For example, combinations of recombinase elements comprising two or more site-specific recombination (SSR) systems may be designed to effect regulated expression and/or removal of trait gene. This coupling of conditional and tissue-specific promoters with two or more site-specific recombinations, such that the conditional expression of one recombinase activates another later in the life cycle, allows their use as a series of genetic switches.

Although SSRs have been used singly as genetic switches, two (or more) SSRs under the control of different constitutive or regulated promoters can be used as a series of genetic switches within a plant's life cycle, such that conditional expression of one recombinase element at one stage activates another recombinase element at a later stage in the same or the subsequent generation. Thus, one can conditionally trigger the process at a convenient developmental stage, such as germination, but get delayed effects at later stages. Trait gene removal may be unlinked or linked to trait gene expression. The latter provides a more stringent control of trait gene expression. One of the key aspects of the invention is that expression of the various recombinase enzymes does not have to occur immediately upon enablement or priming of the recombinase elements (i.e., removal of the stop fragment) but are rather controlled solely by the choices of the respective promoters.

Accordingly the invention provides a trait removal construct comprising:
  a) A first recombinase element having the general structure:
    $P_1$-R and;
  b) A second recombinase element selected from the group of general structures consisting of K-TG, and RS-K-TG-RS;
  wherein,
    (i) $P_1$ is a first promoter;

(ii) R is a recombinase coding sequence and 3' region
(iii) TG is a transgene;
(iv) RS is a recombinase site responsive to the recombinase
(v) K is selected from the group consisting of;
  1) $P_2$-RS-STP-RS and
  2) $P_2$
  wherein $P_2$ is a second promoter, RS is a recombinase site responsive to the recombinase and STP is a stop fragment;
wherein $P_1$ and $P_2$ are operably linked to their down stream elements and wherein $P_1$ is activated prior to or at the same time as $P_2$ in the plant life cycle and wherein expression of the recombinase results in excision of any element contained between the recombinase site responsive to the recombinase.

In an alternate embodiment the invention provides a trait removal construct comprising:
a) a first recombinase element selected from the group of general structures consisting of:
  $P_1$-$R_1$ and $P_1$-$R_2$, and;
b) a second recombinase element having the general structure $RS_2$-K-TG-$RS_2$;
wherein,
  (i) $P_1$ is a first promoter;
  (ii) $R_1$ is a first recombinase coding sequence and 3' region;
  (iii) $R_2$ is a second recombinase coding sequence and 3' region;
  (iv) $RS_2$ is a second recombinase site responsive to the second recombinase;
  (v) TG is a transgene sequence and 3' region;
  (vi) K is selected from the group consisting of;
    1) $P_2$-$RS_1$-STP-$RS_1$ and
    2) $P_2$-$RS_1$-TG
    wherein $P_2$ is a second promoter, $RS_1$ is a first recombinase site responsive to the first recombinase, STP is a stop fragment and TG is a transgene sequence and 3' region;
wherein $P_1$ and $P_2$ are operably linked to their down stream elements, and wherein P1 is activated earlier than or at the same time as P2 in the plant life cycle, and wherein expression of the first recombinase results in excision of any element contained between the first recombinase sites responsive to the first recombinase and expression of the second recombinase results in excision of any element contained between the second recombinase sites responsive to the second recombinase.

In another embodiment the invention provides a trait removal construct comprising:
a) a first recombinase element selected from the group of general structures consisting of $P_1$-$R_1$ and $RS_2$-$P_1$-$R_1RS_2$;
b) a second recombinase element selected from the group of general structures Z-Y and $RS_2$-Z-Y-$RS_2$;
c) a third recombinase element selected from the group of general structures Q-X and $RS_2$-Q-X-$RS_2$;
Wherein:
  (i) $P_1$ is a first promoter;
  (ii) $R_1$ is a first recombinase coding sequence and 3' region;
  (iii) $RS_2$ is a second recombinase site responsive to a second recombinase;
  (iv) Z has the general formula, $P_2$-$RS_1$-STP-$RS_1$,
    wherein $P_2$ is a second promoter, RS is a first recombinase site responsive to a first recombinase, and STP is a stop fragment;
  (v) Y is selected from the group consisting of $R_2$ and TG
    wherein $R_2$ is a second recombinase coding sequence and 3' region and TG is a transgene sequence and 3' region;
  (vi) Q has the general formula $P_3$-RS-STP-RS,
    wherein $P_3$ is a third promoter, RS is a recombinase site selected from the group consisting of $RS_1$ and $RS_2$ and STP is a stop fragment;
  (vii) X is selected from the group consisting of TG and R
    Wherein TG is a transgene sequence and 3' region and R is a recombinase coding sequence and 3' region selected from the group consisting of $R_1$ and $R_2$;
  wherein $P_1$, $P_2$ and $P_3$ are operably linked to their down stream elements and wherein P1 is activated earlier than P2 in the plant life cycle, and wherein P2 is activated earlier than P3 in the plant life cycle, and wherein expression of the first recombinase results in excision of any element contained between the first recombinase sites responsive to the first recombinase and expression of the second recombinase results in excision of any element contained between the second recombinase sites responsive to the second recombinase.

The constructs of the present invention will comprise a first promoter selected from the group consisting of:
  (a) constitutive plant promoters;
  (b) plant tissue-specific promoters;
  (c) plant development-specific promoters;
  (d) inducible plant promoters;
  (e) viral promoters;
  (f) male germline-specific promoters;
  (g) female germline-specific promoters;
  (h) male/female germline-specific promoters;
  (i) flower-specific promoters; and
  (j) vegetative shoot apical meristem-specific promoters.

Where the constructs of the present invention contain a second promoter that promoter is selected from the group consisting of: constitutive plant promoters; plant tissue-specific promoters; plant development stage-specific promoters; inducible plant promoters; and viral promoters.

Where the constructs of the present invention comprise a transgene for expression the transgene is selected from the group consisting of: genes encoding a transformation marker; genes encoding a morphological trait; genes conveying sterility; genes conveying specific phenotype on a plant or plant cell; and hormone biosynthetic genes.

Additionally the different components of the invention are heritable independently and may be introduced together into a transgenic plant or brought together by crossing transgenic plants carrying the separate components, such as by the method to produce TopCross® high oil corn seed (U.S. Pat. No. 5,704,160). Also provided are methods of making the expression cassettes and methods of using them to produce transformed plant cells having an altered genotype and/or phenotype.

BRIEF DESCRIPTION OF FIGURES AND SEQUENCE DESCRIPTIONS

Figure 1:
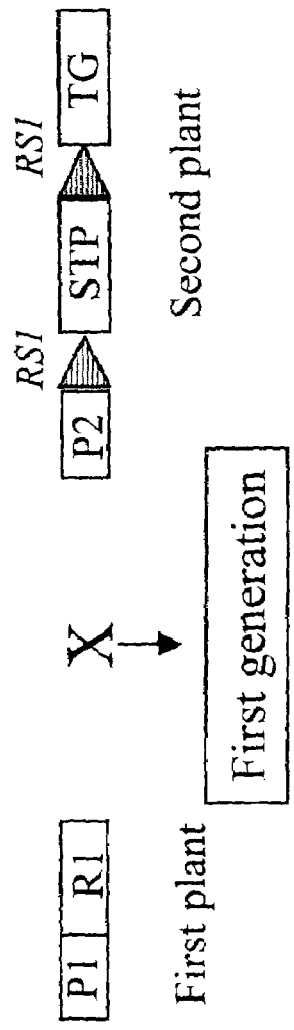
FIG. 1 illustrates a scheme for the use of a single site-specific recombinase system for the conditional expression of a transgene gene in a first generation plant.
Figure 1:
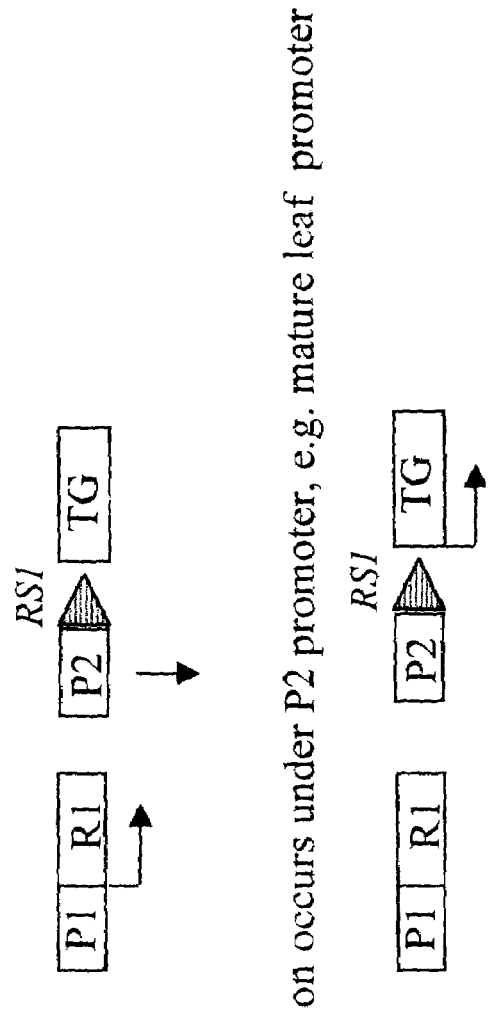

The following sequence descriptions and sequences listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

SEQ ID NO:1 is the primer used as P298.
SEQ ID NO:2 is the primer used as P299.
SEQ ID NO:3 is the primer used as P192.
SEQ ID NO:4 is the primer used as P194.
SEQ ID NO:5 is the primer used as P198.
SEQ ID NO:6 is the primer used as P227.
SEQ ID NO:7 is the primer used as P228.
SEQ ID NO:8 is the primer used as PH785 for PCR amplification of the *Arabidopsis* Apetala 3 (AP3) promoter.
SEQ ID NO:9 is the primer used as PH786 for PCR amplification of the *Arabidopsis* Apetala 3 (AP3) promoter.
SEQ ID NO:10 is the primer used as PH783 for PCR amplification of the BCP1 promoter.
SEQ ID NO:1 is the primer used as PH784 for PCR amplification of the BCP1 promoter.
SEQ ID NO:12 is the primer used as PH788 for PCR amplification of the *Arabidopsis* Erecta (ER) promoter.
SEQ ID NO:13 is the primer used as PH790 for PCR amplification of the *Arabidopsis* Erecta (ER) promoter.
SEQ ID NO:14 is the primer used as PH795 for PCR amplification of the TA29 promoter from plasmid pTZALG.
SEQ ID NO:15 is the primer used as PH815 for PCR amplification of the TA29 promoter from plasmid pTZALG.
SEQ ID NO:16 is the primer used as P321 for PCR amplification of the *Arabidopsis* Pistilata (PI) promoter.
SEQ ID NO:17 is the primer used as P322 for PCR amplification of the *Arabidopsis* Pistilata (PI) promoter.
SEQ ID NO:18 is the primer used as PH806 for PCR amplification of the *Arabidopsis* Heat Shock (HSP) promoter 18.2.
SEQ ID NO:19 is the primer used as PH807 for PCR amplification of the *Arabidopsis* Heat Shock (HSP) promoter 18.2.
SEQ ID NO:20 is the primer used as P355 for PCR amplification of the *Arabidopsis* Apetala 1 (AP1) promoter.
SEQ ID NO:1 is the primer used as P356 for PCR amplification of the *Arabidopsis* Apetala 1 (AP1) promoter.
SEQ ID NO:22 is the primer used as P353 for PCR amplification of the *Arabidopsis* Agamous (AG) promoter.
SEQ ID NO:23 is the primer used as P354 for PCR amplification of the *Arabidopsis* Agamous (AG) promoter.

DETAILED DESCRIPTION OF THE INVENTION

The present invention provides constructs and methods for the conditional or regulated expression or excision of transgenes in plants by employing one or more site-specific recombinase systems and transgenes under the control of a variety of constitutive, inducible, tissue specific or development-specific promoters. Regulated expression of genetic traits is useful in plant breeding and agronomic applications. Additionally transgene removal or excision from germline (pollen and/or seed) can be used not only for its containment in the production field but also for obtaining marker-free transgenics. Persistence of transformation marker, which is required to identify the rare transformed cells, in transgenic plants may be undesirable because of regulatory concerns/requirements, its detrimental effect on transgenic plants, and/or it prevents recurrent use of the marker for stacking trait transgenes. The following terms and definitions shall be used to fully understand the specification and claims.

"Gene" refers to a nucleic acid fragment that expresses mRNA, functional RNA, or specific protein, including regulatory sequences. The term "native gene" refers to gene as found in nature. The term "chimeric gene" refers to any gene that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature. A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism.

"Coding sequence" refers to a DNA or RNA sequence that codes for a specific amino acid sequence and excludes the non-coding sequences. The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences which may be a combination of synthetic and natural sequences. As is noted above, the term "suitable regulatory sequences" is not limited to promoters, however, some suitable regulatory sequences useful in the present invention will include, but are not limited to constitutive plant promoters, plant tissue-specific promoters, plant developmental stage-specific promoters, inducible plant promoters and viral promoters.

The "3' region" means the 3' non-coding regulatory sequences located downstream of a coding sequence. This DNA can influence the transcription, RNA processing or stability, or translation of the associated coding sequence (e.g. for a recombinase, a transgene, etc.).

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions.

"Conditionally activating" refers to activating a transgene that is normally not expressed. In context of this invention it refers to expression of recombinase R1 either by a cross or, if it is inducible, also by an inducer.

"Constitutive expression" refers to expression using a constitutive or regulated promoter. "Conditional" and "regulated expression" refer to expression controlled by regulated promoter. "Transient" expression in context of this invetion refers to expression only in specific developmental stages or tissue in one or two generation.

"Constitutive promoter" refers to promoters that direct gene expression in all tissues and at all times. "Regulated promoter" refers to promoters that direct gene expression not constitutively but in a temporally- and/or spatially-regulated manner and include tissue-specific, developmental stage-specific, and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered; numerous examples may be found in the compilation by Okamuro et al., *Biochemistry of Plants* 15:1–82, 1989. Since in most cases the exact boundaries of regulatory sequences have not been completely defined, DNA fragments of different lengths may have identical promoter activity. Typical regulated promoters useful in plants include but are not limited to safener-inducible promoters, promoters derived from the tetracycline-inducible system, promoters derived from salicylate-inducible systems, promoters derived from alcohol-inducible systems, promoters derived from glucocorticoid-inducible system, promoters derived from pathogen-inducible systems, and promoters derived from ecdysome-inducible systems.

"Tissue-specific promoter" refers to regulated promoters that are not expressed in all plant cells but only in one or more cell types in specific organs (such as leaves, shoot apical meristem, flower, or seeds), specific tissues (such as embryo or cotyledon), or specific cell types (such as leaf parenchyma, pollen, egg cell, microspore- or megaspore mother cells, or seed storage cells). These also include "developmental-state specific promoters" that are temporally regulated, such as in early or late embryogenesis, during fruit ripening in developing seeds or fruit, in fully differentiated leaf, or at the onset of senescence. It is understood that the developmental specificity of the activation of a promoter and, hence, of the expression of the coding sequence under its control, in a transgene may be altered with respect to its endogenous expression. For example, when a transgene under the control of a floral promoter is transformed into a plant, even when it is the same species from which the promoter was isolated, the expression specificity of the transgene will vary in different transgenic lines due to its insertion in different locations of the chromosomes.

"Non-specific expression" refers to constitutive expression or low level, basal ('leaky') expression in nondesired cells, tissues, or generation.

"Inducible promoter" refers to those regulated promoters that can be turned on in one or more cell types by a stimulus external to the plant, such as a chemical, light, hormone, stress, or a pathogen.

"Promoter activation" means that the promoter has become activated (or turned "on") so that it functions to drive the expression of a downstream genetic element. Constitutive promoters are continually activated. A regulated promoter may be activated by virtue of its responsiveness to various external stimuli (inducible promoter), or developmental signals during plant growth and differentiation, such as tissue specificity (floral specific, anther specific, pollen specific seed specific etc) and development-stage specificity (vegetative or floral shoot apical meristem-specific, male germline specific, female germline specific etc).

"Operably-linked" refers to the association of nucleic acid sequences on a single nucleic acid fragment so that the function of one is affected by the other. For example, a promoter is operably-linked with a coding sequence or functional RNA when it is capable of affecting the expression of that coding sequence or functional RNA (i.e., that the coding sequence or functional RNA is under the transcriptional control of the promoter). Coding sequences can be operably-linked to regulatory sequences in sense or antisense orientation. "Unlinked" means that the associated genetic elements are not closely associated with one another and function of one does not affect the other.

"Expression" refers to the transcription and stable accumulation of sense (mRNA) or functional RNA. Expression may also refer to the production of protein. "Overexpression" refers to the level of expression in transgenic organisms that exceeds levels of expression in normal or untransformed organisms.

"Altered levels" refers to the level of expression in transgenic organisms that differs from that of normal or untransformed organisms.

The term "altered plant trait" means any phenotypic or genotypic change in a transgenic plant relative to the wild-type or non-transgenic plant host.

"Transcription Stop Fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation Stop Fragment" refers to nucleotide sequences that contain one or more regulatory signals, such as one or more termination codons in all three frames, capable of terminating translation. Insertion of translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

"Stop fragment" or "Blocking fragment" refers to a DNA fragment that is flanked by site-specific sequences that can block the transcription and/or the proper translation of a coding sequence resulting in an inactive transgene. When the blocking fragment contains polyadenylation signal sequences and other sequences encoding regulatory signals capable of terminating transcription it can block the transcription of a coding sequence when placed in the 5' non-translated region, i.e., between the transcription start site and the ORF. When inserted in the coding sequence a blocking fragment can block proper translation by disrupting its open reading frame. DNA rearrangement by site-specific recombination can restore transcription and/or proper translatability. For example, excision of the blocking fragment by site-specific recombination leaves behind a site-specific sequence that allows transcription and/or proper translatability. A Transcription or Translational Stop Fragment will be considered a blocking fragment. A "stop fragment" can also block transcription by disrupting the gene in the non-transcribed region, for example by its presence and/or orientation in promoter sequences either between the upstream promoter elements and the "TATA" box or between the TATA box and the transcription start site.

This process of excision of the stop fragment or blocking fragment will be referred to herein as "unblocking". When the blocking fragment is removed from the DNA by site-specific recombination, it will be appreciated by one skilled in the art that a site-specific sequence remains which can be transcribed and/or translated properly.

"Priming" or "enabling" refers to the removal of blocking sequences upstream of a promoter and/or gene, such that the gene can become activated in response to the appropriate environmental cue, stage of development, or presence in a specific tissue/cell type. When a genetic element is enabled or primed by the removal of a blocking fragment, the promoter element may or may not be free to drive the expression of the downstream element. For example, a genetic construct comprising an inducible promoter separated by a stop fragment from a down stream gene to which it is operably linked, will be primed by the removal of the stop fragment, however will not express the downstream element until it is activated or induced. Thus, activation of a blocked gene will require enabling it and activation of the promoter driving the gene.

"Recombinase element" refers to a DNA element comprising a promoter operably linked to a gene encoding a site-specific recombinase, or to other genetic elements flanked by site-specific recombinase sequences. Recombinase elements of the present invention may optionally contain blocking or stop fragments to allow for more highly regulated gene expression.

The term "floxed" will refer to the flanking of a genetic element with tandemly (i.e., directly, repeated) site-specific sequences. The floxed element may be recombinase element or any other genetic element.

The term "recombinase" refers to enzyme(s) that carry out site-specific recombination that alters the DNA structure and includes transposases, lambda integration/excision enzymes, as well as site-specific recombinases. Well-known examples of recombinases can be found in Cre-lox, FLP/FRT, R/RS, Gin/gix, a pSR1 system, a cer system, and a fim system (for example, N. L. Craig, *Annu Rev. Genet.*, vol. 22, p. 17, 1988; Odell et al., *Use of site-specific recombination systems in plants. Homologous Recomb. Gene Silencing Plants* (1994), 219–70. Editor(s): Paszkowski, Jerzy. Publisher: Kluwer, Dordrecht, Germany). Additionally, site-specific recombination systems have been identified in microorganisms such as phage, bacterium (e.g., *E. coli*), yeast and the like. This includes the *E. coli* lambda att P system (Zubko et al. (2000) *Nature Biotechnology* 18:442) integration and excision and the *Streptomyces* phage C31 integrase (Groth et al. (2000) *Proc. Natl. Acad. Sci. USA* 97:5995). When the site-specific recombination system separated from these microorganisms with the use of a Cre/lox system derived from P1 phage (WO 93/01283) is introduced into organisms (including plants) different from the organism from which this system had been derived, it behaves in the same way as in the original organism. The site-specific recombination system of yeast (*Zygosaccharomyces rouxii*) (pSR1 system (H. Matsuzaki et al., *J. Bacteriology*, vol. 172, p. 610, 1990)) can also be used in accordance with the present invention. This pSR1 system also maintains its inherent function in higher plants (H. Onouchi et al., *Nucleic Acid Res., vol.* 19, p. 6373, 1991).

"Recombinase site" or "site-specific recombinase sequence" means a DNA sequence that a recombinase will recognize and bind to. It will be appreciated that this may be a wild type or mutant recombinase site, as long as functionality is maintained and the recombinase enzyme may still recognize the site, bind to the DNA sequence, and catalyze the recombination between two adjacent recombinase sites.

"Trait removal construct" is defined herein as any assembly of DNA constructs comprising (at least): a recombinase element, site specific recombinase sites responsive to the recombinase enzyme, and a transgene. The trait removal construct becomes functional upon the introduction of each element into a single organism, either by co-transformation, sequential transformations, or genetic crosses after single transformation in a plant.

"Production tissue" refers to mature, harvestable tissue consisting of non-dividing, terminally-differentiated cells. It excludes young, growing tissue consisting of germline, meristematic, and not-fully-differentiated cells.

"Germline" refers to cells that are destined to be gametes. Thus, the genetic material of germline cells is heritable.

"Common germline" refers to all germline cells prior to their differentiation into the male and female germline cells and, thus, includes the germline cells of developing embryo, vegetative SAM, floral SAM, and flower. Thus, site-specific excision in common germline results in excision from both male and female gametes.

"Male germline" refers to cells of the sporophyte (anther primordial anther, microspore mother cells) or gametophyte (microspore, pollen) that are destined to be male gametes (sperms) and the male gametes themselves.

"Female germline" refers to cells of the sporophyte (pistil primordia, pistil, ovule, macrospore mother cells) or gametophyte (macsrospore, egg cell) that are destined to be female gametes or the female gametes themselves.

"Somatic" cells are all other cells in the organism that are not germline cells.

"Common germline" promoter refers to a promoter that is activated in germline cells prior to their differentiation into the male and female germlines. It also refers to a promoter that is activated in both male and female germline cells and to a set of promoters, one specific to the male germline and the other to the female germline. Thus, site-specific excision in common germline results in excision from both male and female gametes.

"Floral common germline" promoter refers to a promoter of flower or flower primordia genes whose expression occurs in "common germlines". It does not include male germline or female germline promoters, which are also expressed in the flower.

"Male germline" promoter refers to a promoter whose expression occurs in male not female germline in the flower.

"Female germline" promoter refers to a promoter whose expression occurs in female not male germline in the flower.

"Flower" or "floral"-specific promoter refers to a promoter whose expression occurs in the flower or flower primordia. They include floral common germline, male germline, and female germline promoters.

"Genetically linked" refers to physical linkage of transgene such that they co-segregate in progeny.

"Genetically unlinked" refers to the lack of physical linkage of transgene such that they do not co-segregate in progeny.

"Seed-specific promoter refers to promoter that is expressed only in the seed.

"Plant developmental stage-specific promoter" refers to a promoter that is expressed not constitutively but at specific plant developmental stage or stages Plant development goes through different stages and in context of this invention the germline goes different developmental stages starting, say, from fertilization through development of embryo, vegetative shoot apical meristem, floral shoot apical meristem, anther and pistil primordial anther and pistil, micro- and macrospore mother cells, and macrospore (egg) and microspore (pollen).

"Vegetative shoot apical meristem' refers to the cells found in the shoot apex of vegetative shoots that give rise to leaves and shoots.

"Floral shoot apical meristem' refers to the cells found in the shoot apex of floral meristem shoots that give rise to flowers and inflororescenes.

"Morphological trait" refers to traits of morphology, such as shoots, roots, calli, tumors, flowers, or leaves "Tumorigenic" genes refers to genes that cause plant tumors, such as the T-DNA genes of *Agrobacterium tumefaciens*.

"Root inducing" genes refers to genes, such rol A, B, and C genes of *Agrobacterium rhizogenes*, that cause root formation.

The term "Lethal gene that block development" refers to a gene that express a toxin, such as alpha chain of diptheria toxin, barnase, or interfers with normal plant development, such as rolB (Roder et al. (1994) Mol. Gen. Genet. 243:32). It also includes transgenes that silence or co-suppress plant gens required for normal development (see Chuang CF, Meyerowitz EM (2000) *Specific and heritable genetic interference by double-stranded RNA in Arabidopsis thaliana. Proc Natl Acad Sci USA*. 97:4985–90)

"Conditional and transient expression" refers to expression of a trait gene only in the selected generation or two. In context of this invention, expression is triggered in first generation and upon useful trait expression, the trait gene is removed from the germline.

Restoring male fertility" refers to removing a male sterility gene by excision or counteracting it by the expression of a suppressor that can be either a transgene for silencing the male sterility gene or a transgene that encode a protein that cointeracts the male sterility factor, such as barstar against barnase ichiels, F., and M. Williams, 1998, Improved barstar gene and its expression in male-sterile barnase-producing plants to restore fertility, PCT Int. Appl., WO, (Plant Genetic Systems, N. V., Belg.; Michiels, Frank; Williams, Mark)., p. 54 pp.

"Synthetic anther promoter" refers to G9/SGB6 hybrid promoter (U.S. Pat. Nos. 5,470,359; 5,837,850).

"Pollen-specific: promoters refers to promoters that are only expressed in pollen, such as LAT52 Twell et al. (1998) *Trends in Plant Sciences* 3:305.

"Sterility" means the inability of a plant to reproduce sexually or to set seeds. In cross pollinating plants it will include inability to form a functional pollen as well as inability to set seeds. Sterility can also result from abnormal plant development that prevents flower formation. A "sterility gene" refers to any gene that conveys sterility to the plant and includes genes that prevent both pollen formation and seed set such as by preventing flower formation. "Male sterility" means the inability of a plant to produce functional pollen as a consequence of mechanical or hand detasseling, incorporation of genetic male sterility, or by other means. "Female sterility" means the inability of a plant to set seeds.

Male sterility result from the expression of the male sterility gene in diploid cells (sporophytic), haploid (ganetophytic) cells, or both types of cells. Gametophytic male sterility refers to a gene whose expression occurs only in the pollen, for example expression of barnase or the alpha chain of diptheria toxin under pollen-specific promoter.

"Gametophytic male sterility" refers to sterility that is expressed only in pollen.

"Gametophytic male fertility restorer" a transgene that restores fertility by removing or suppressing the male sterility gene.

"Barnase" and "Barstar" refer to a RNase toxin and its antidote as described by Michiels, F., and M. Williams, 1998, Improved barstar gene and its expression in male-sterile barnase-producing plants to restore fertility, PCT Int.

Appl., WO, (Plant Genetic Systems, N. V., Belg.; Michiels, Frank; Williams, Mark)., p. 54 pp.

"Activating transgene" refers to expression of a transgene. In context of this invention, it refers to both enabling a blocked gene or enabling a blocked gene followed by activation of its promoter.

"Transformation" refers to the transfer of a foreign gene into the genome of a host organism. Examples of methods of plant transformation include *Agrobacterium*-mediated transformation (De Blaere et al.(1987) *Meth. Enzymol.* 143:277) and particle-accelerated or "gene gun" transformation technology (Klein et al.(1987) *Nature* (London) 327:70–73; U.S. Pat. No. 4,945,050). The terms "transformed", "transformant" and "transgenic" refer to plants or calli that have been through the transformation process and contain a foreign gene integrated into their chromosome. The term "untransformed" refers to normal plants that have not been through the transformation process.

"Stably transformed" refers to cells that have been selected and regenerated on a selection media following transformation.

"Genetically stable" and "heritable" refer to chromosomally-integrated genetic elements that are stably maintained in the plant and stably inherited by progeny through successive generations.

"Wild-type" refers to the normal gene, virus, or organism found in nature without any known mutation.

"Genome" refers to the complete genetic material of an organism.

"Genetic trait" means a genetically determined characteristic or condition, which is transmitted from one generation to another. "Homozygous" state means a genetic condition existing when identical alleles reside at corresponding loci on homologous chromosomes. In contrast, "heterozygous" state means a genetic condition existing when different alleles reside at corresponding loci on homologous chromosomes. A "hybrid" refers to any offspring of a cross between two genetically unlike individuals. "Inbred" or "inbred lines" or "inbred plants" means a substantially homozygous individual or variety. This results by the continued mating of closely related individuals, especially to preserve desirable traits in a stock.

The term "ortholog" or "orthologous genes" refer to genes related by common phylogenetic descent. Orthologous genes are those genes from one species which corresponds to a gene in another species that is related via a common ancestral species (a homologous gene), but which has evolved to become different from the gene of the other species.

"Selfing" or "self fertilization" refers to the transfer of pollen from an anther of one plant to the stigma (a flower) of that same said plant. Selfing of a hybrid (F1) results in a second generation of plants (F2)

"TopCross® high oil corn seed method" refers to a commercial method of making hybrid corn seeds in the field, as described, for example, in U.S. Pat. No. 5,704,160. A "TopCross® pollinator refers to the parent line of the cross that provides the pollen.

The term "sporophyte" means the diploid phase or cells of a plant.

The term "gametophyte" means haploid phase or cells of a plant. This is the stage in a plant's life cycle between meiosis and fertilization. The male gametophyte includes the haploid phase or cells of the pollen and the female gametophyte includes the haploid phase or cells of the egg cell.

The term "plant life cycle" means a complete sequence of developmental events in the life of a plant, such as from fertilization to the next fertilization or from flowering in one generation to the next.

"Primary transformant" and "$T_0$ generation" refer to transgenic plants that are of the same genetic generation as the tissue which was initially transformed (i.e., not having gone through meiosis and fertilization since transformation).

"Secondary transformants" and the "$T_1$, $T_2$, $T_3$, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

The term "generation" means a plant life cycle starting from fertilization to fertilization. In the context of this invention, a "first generation plant" is defined as the plant in which the first recombination event occurs, while a "second generation plant" is the progeny seed and plant of the first generation plant.

A "restorer gene" is defined herein as a gene whose expression restores fertility. A gametophyte fertility restorer gene refers to genes whose expression overcome gametophytic sterility, such as a barstar gene (Michiels, F., and M. Williams, 1998, Improved barstar gene and its expression in male-sterile barnase-producing plants to restore fertility, PCT Int. Appl., WO, (Plant Genetic Systems, N. V., Belg.; Michiels, Frank; Williams, Mark)., P. 54 pp.).

The following abbreviations will be used herein:

"STP" is the abbreviation for stop fragment or blocking fragment.

"AP1" is the abbreviation for *Arabidopsis* Apetala 1 gene (Liljegren et al, (1999) *The Plant Cell* 111:1007.)

"AG" is the abbreviation for *Arabidopsis* agamous gene (Yanofsky et al. 91990) *Nature* 346:35).

"PI" is the abbreviation for *Arabidopsis* Pistillata gene (Goto and Meyerowitz (1994) *Genes and development* 8:1548–1560).

"LFY" is the abbreviation for *Arabidopsis* Leafy gene (Nilsson et al. (1998) *The Plant Journal* 15:799–804).

"ANT" is the abbreviation for *Arabidopsis* Aintegumenta gene (Mizukami and Fischer (2000) *Proc. Natl. Acad. Sci. USA* 97:942–947).

"CLV3" is the abbreviation for *Arabidopsis* Clavata 3 gene (Fletcher et al. (1999) *Science* 283:1911–1914).

"WUS" is the abbreviation for *Arabidopsis* Wushel gene (Mayer et al. (1998) *Cell* 95(6), 805–815).

"STM" is the abbreviation for, *Arabidopsis* Shoot Meristemless gene (Long et al. (1996) *Nature* 379:66–69).

"rol C" is the abbreviation for the root locus C gene that causes root formation (see Constantino et al. (1994) *Gentics* 94:203).

"IPT" is the abbreviation for the isopentyl transferase gene (Ebumina et al. (1997;) *Proc. Natl. Acad. Sci. USA* 94:2117–2121).

"KNAT" is the abbreviation for the a Knox class of genes (see Reiser et al. (2000) *Plant Mol. Biol.* 42:151–166').

"Lec1" is the abbreviation for *Arabidopsis* Leafy Cotyledon 1 (Lotan et al, 1998. *Cell* 93: 1195–1205) gene.

"OSHI" is the abbreviation for a rice homeobox gene (Sentoku et al. (2000) *Developmental Biology* 220:358–364).

"Kn1" is the abbreviation for corn Knotted 1 gene (Vollbrecht, E. et al. (1991) *Nature* 350:241–243).

"Gmf" means gametophytic male fertile.

"Gms" means gametophytic male sterile.

"TG" is the abbreviation for transgene.

"SAM" is the abbreviation for shoot apical meristem. SAM can be vegetative or floral.

"SSR" is the abbreviation for site-specific recombination.

"SAP is the abbreviation for Synthetic anther promoter as described in U.S. Pat. Nos. 5,470,359; 5,837,850.

"HSP" is the abbreviation for heat shock protein.

The present invention provides constructs and methods for the conditional or regulated expression or excision of transgenes in plants by employing one or more site-specific recombinase systems and transgenes under the control of a variety of constitutive, inducible, tissue specific or development-specific promoters. The invention makes use of a variety of constructs referred to herein as recombinase elements. Each recombinase element comprises at least one promoter functional in a plant cell. Additionally the recombinase element may comprise a number of other components including sequence encoding a site specific recombinase or a transgene or may comprise a stop fragment or site-specific sequences responsive to a recombinase. The recombinase elements are introduced into plants in a variety of combinations so as to provide for the conditional expression or excision of specific genetic traits encoded by the transgenes. By matching promoters, responsive to various inducers, plant tissues or plant developmental states with the recombinase systems, stop fragments and transgenes, virtually any trait may be expressed or excised at any plant development stage or in any plant generation.

The present system of gene expression has several advantages over current methods. For example, regulated expression under some current promoters may result in non-specific or "leaky" expression.

Promoters

The present invention makes use of a variety of plant promoters to drive the expression of either a recombinase or a transgene as part of the recombinase elements of the invention.

Regulated expression of transgene expression is possible by placing the transgene or recombinase system under the control of promoters that may be conditionally regulated. Any promoter functional in a plant will be suitable including but not limited to constitutive plant promoters, plant tissue-specific promoters, plant development-specific promoters, inducible plant promoters, viral promoters, male germline-specific promoters, female germline-specific promoters, flower-specific promoters, and vegetative shoot apical meristem-specific promoters.

Several tissue-specific regulated genes and/or promoters have been reported in plants. These include genes encoding the seed storage proteins (such as napin, cruciferin, beta-conglycinin, and phaseolin), zein or oil body proteins (such as oleosin), or genes involved in fatty acid biosynthesis (including acyl carrier protein, stearoyl-ACP desaturase, and fatty acid desaturases (fad 2-1)), and other genes expressed during embryo development (such as Bce4, see, for example, EP 255378 and Kridl et al., *Seed Science Research* (1991) 1:209–219). Particularly useful for seed-specific expression is the pea vicilin promoter (Czako et al., *Mol. Gen. Genet.* (1992), 235(1), 33–40). Other useful promoters for expression in mature leaves are those that are switched on at the onset of senescence, such as the SAG promoter from *Arabidopsis* (Gan et al., "Inhibition of leaf senescence by autoregulated production of cytokinin", *Science* (Washington, D.C.) (1995), 270 (5244), 1986–8).

A class of fruit-specific promoters expressed at or during anthesis through fruit development, at least until the beginning of ripening, is discussed in U.S. Pat. No. 4,943,674, the disclosure of which is hereby incorporated by reference. cDNA clones that are preferentially expressed in cotton fiber have been isolated (John et al., Gene expression in cotton (*Gossypium hirsutum* L.) fiber: cloning of the mRNAs, *Proc. Natl. Acad. Sci.* (U.S.A. (1992), 89 (13), 5769–73). cDNA clones from tomato displaying differential expression during fruit development have been isolated and characterized (Mansson et al., *Mol. Gen. Genet.* (1985) 200:356–361; Slater et al., *Plant Mol. Biol.* (1985) 5:137–147). The promoter for polygalacturonase gene is active in fruit ripening. The polygalacturonase gene is described in U.S. Pat. No. 4,535,060 (issued Aug. 13, 1985), U.S. Pat. No. 4,769,061 (issued Sep. 6, 1988), U.S. Pat. No. 4,801,590 (issued Jan. 31, 1989) and U.S. Pat. No. 5,107,065 (issued Apr. 21, 1992), which disclosures are incorporated herein by reference.

Mature plastid mRNA for psbA (one of the components of photosystem II) reaches its highest level late in fruit development, in contrast to plastid mRNAS for other components of photosystem I and II which decline to nondetectable levels in chromoplasts after the onset of ripening (Piechulla et al., *Plant Mol. Biol.* (1986) 7:367–376). Recently, cDNA clones representing genes apparently involved in tomato pollen (McCormick et al., *Tomato Biotechnology* (1987) Alan R. Liss, Inc., New York) and pistil (Gasser et al., *Plant Cell* (1989), 1:15–24) interactions have also been isolated and characterized.

Other examples of tissue-specific promoters include those that direct expression in leaf cells following damage to the leaf (for example, from chewing insects), in tubers (for example, patatin gene promoter), and in fiber cells (an example of a developmentally-regulated fiber cell protein is E6 (John et al., Gene expression in cotton (*Gossypium hirsutum* L.) fiber: cloning of the mRNAs, *Proc. Natl. Acad. Sci. U.S.A.* (1992), 89(13), 5769–73)). The E6 gene is most active in fiber, although low levels of transcripts are found in leaf, ovule and flower.

The tissue-specificity of some "tissue-specific" promoters may not be absolute and may be tested by one skilled in the art using the diphtheria toxin sequence. One can also achieve tissue-specific expression with "leaky" expression by a combination of different tissue-specific promoters (Beals et al., (1997) *Plant Cell*, vol 9, 1527–1545). Other tissue-specific promoters can be isolated by one skilled in the art (see U.S. Pat. No. 5,589,379).

Germline specific promoters, responsive to male, female, or both male-female specific cell lineages are also useful in the present invention. For instance transgenes can be expressed or removed from pollen by site-specific recombinase expression under the control of male germline-specific genes in anther primordia genes, such as *Arabidopsis* Apetalla 3 and Pistilata (PI) or their orthologs from other plant species, in sporophytic anther tissue (leg. Bcp I and TA29 promoters, or gametophytic pollen. Similarly, transgenes can be expressed or removed from ovules by site-specific recombinase expression under the control of female germline-specific genes in ovule primordia. Transgenes can be expressed or removed from both male- and female-specific germlines by expression of site-specific recombinase gene under the control of promoter for genes common to both male and female lineages in flower, such as *Arabidopsis* agamous gene or its orthologs in other species, in floral meristem, such as *Arabidopsis* Apetala 1, Leafy, and Erecta or their orthologs from other species, and in vegetative shoot apical meristem, such as *Arabidopsis* WUSCHEL (WUS) and SHOOT MERISTEMLESS (STM) or their orthologs from other species. Promoters of shoot apical meristem are especially useful for removing or expressing transformation marker genes early in tissue-culture following selection or in planta following a transformation phenotype.

Similarly, several inducible promoters ("gene switches") have been reported. Many are described in the review by Gatz (*Current Opinion in Biotechnology*, 1996, vol. 7, 168–172; Gatz, C. Chemical control of gene expression, *Annu. Rev. Plant Physiol. Plant Mol. Biol.* (1997), 48, 89–108). These include tetracycline repressor system, Lac repressor system, copper-inducible systems, salicylate-inducible systems (such as the PR1a system), glucocorticoid- (Aoyama T. et al., *N—H Plant Journal* (1997) vol 11:605–612) and ecdysome-inducible systems. Also, included are the benzene sulphonamide-(U.S. Pat. No. 5,364,780) and alcohol-(WO 97/06269 and WO 97/06268)-inducible systems and glutathione S-transferase promoters. Other studies have focused on genes inducibly regulated in response to environmental stress or stimuli such as increased salinity, drought, pathogen, and wounding. (Graham et al., *J. Biol. Chem.* (1985) 260:6555–6560; Graham et al., *J. Biol. Chem.* (1985) 260:6561–6554) (Smith et al., *Planta* (1986) 168:94–100). Accumulation of a metallocarboxypeptidase-inhibitor protein has been reported in leaves of wounded potato plants (Graham et al., *Biochem Biophys Res Comm* (1981) 101:1164–1170). Other plant genes have been reported to be induced methyl jasmonate, elicitors, heat-shock, anerobic stress, or herbicide safeners.

Site-Specific Recombinase Systems

The present invention provides site-specific recombinase systems for use in the regulated expression or excision of transgenes. A site-specific recombination system consists of two elements, (1) a recombination site (corresponding to the removable DNA element of the present invention) having a characteristic DNA sequence, and (2) an enzyme that binds to the DNA sequence specifically and catalyzes the recombination between DNA sequences if two or more of the sequences exist (recombinase). When the two DNA sequences are oriented in the same direction at a given interval on the same DNA molecule, the region held by these DNA sequences is excised from the DNA molecule, such as a plasmid, chromosome or the like. When the two DNA sequences are oriented in opposite directions on the same DNA molecule, the region held by these DNA sequences is inverted.

Use of developmentally-regulated or chemically-induced promoters for conditional transgene expression is usually limited either by their insufficient strength in the "fully-on" stage or, more often, by their basal non-specific (i.e., "leaky") expression) in the 'off' stage, depending on the application.

One can increase both the level and specificity of conditional expression by putting the coding sequence of the gene of interest under the control of a strong constitutive or regulated promoter for expression in the production tissue in such a manner that the gene is transcriptionally inactive unless it undergoes a site-specific recombination through the conditional expression of the cognate site-specific recombinase. Thus, conditional expression of the gene of interest is now dependent on the conditional expression of the recombinase. In this manner, determinants for high-level expression and for specificity are separated and one can then focus on the basal non-specific (i.e., "leaky") expression of recombinase. The site-specific sequences and their cognate recombinase enzymes can be from any natural site-specific recombination systems. Well-known examples include Cre-lox, FLP/FRT, R/RS, Gin/gix, a pSR1 system, a cer system, and a fim system (for example, N. L. Craig, *Annu Rev. Genet.*, vol. 22, p. 17, 1988; Odell et al., *Use of site-specific recombination systems in plants. Homologous Recomb. Gene Silencing Plants* (1994), 219–70. Editor(s): Paszkowski, Jerzy. Publisher: Kluwer, Dordrecht, Germany). Additionally, site-specific recombination systems have been identified in microorganisms such as phage, bacterium (e.g., *E. coli*), yeast and the like. When the site-specific recombination system separated from these microorganisms with the use of a Cre/lox system derived from P1 phage (WO 93/01283) is introduced into organisms (including plants) different from the organism from which this system had been derived, it behaves in the same way as in the original organism. The site-specific recombination system of yeast (*Zygosaccharomyces rouxii*) (pSR1 system (H. Matsuzaki et al., *J. Bacteriology*, vol. 172, p. 610, 1990)) can also be used in accordance with the present invention. This pSR1 system also maintains its inherent function in higher plants (H. Onouchi et al., *Nucleic Acid Res.*, vol. 19, p. 6373, 1991).

Since the levels of the recombinase enzyme required are not expected to be high, several "specific" promoters can be used that may otherwise be too weak to express the gene of interest. Furthermore, since site-specific recombination depends on a threshold level of the recombinase, there may be a tolerance for leaky transcription that results in sub-threshold levels of recombinase.

Furthermore, increased "tissue-selectivity" to available regulated promoters is provided by decreasing the efficiency of wild-type Cre-mediated recombination, raising the threshold of recombinase required by using either a mutant site for site-specific recombination and/or a mutant recombinase that are not proficient in recombination. Such mutants are well known, at least for the Cre-lox system. The applicants have shown that when using safener-inducible Cre expression to activate the expression of a transgene (35S: luciferase), the use of a mutant lox site (lox72) and a wild type lox P site in Cre-mediated activation of the transgene reduces the basal activity of the promoter compared to using both wild type lox P sites.

The non-specificity of recombinase expression can be further reduced (i.e., its expression specificity further increased) by other post-transcriptional approaches including: 1) using a chimeric recombinase gene that is poorly translated (such as having a non-ideal context sequence around the initiation codon following Kozak's rule or having additional short ORFs in the 5' untranslated region as in yeast GCN4 mRNA, or having 3' UTR sequences that makes mRNA unstable as described by Pamela Green (Department of Biochemistry, Michigan State University, East Lansing, Mich. 48824–1312, U.S.A.); 2) using a mutant recombinase that has less cellular stability (i.e., shorter half-life). Such mutants could be made by adding PEST sequences (Sekhar et al., *Jrl. Receptor Signal Transduction Res.* 18 (2–3), 113–132 (1998)).

Once a system is developed in a given crop, it can be easily adapted for conditional expression of a variety of target trait genes.

Transgenes

Transgenes of the present invention will be those that convey a desirable phenotype on the transformed plant, or those that encode markers useful in breeding. Particularly useful transgenes will include, but not be limited to genes conveying specific phenotype on a plant or plant cell, genes encoding a transformation marker, genes encoding a morphological trait, genes conveying sterility, and hormone biosynthetic genes.

Transgenes can encode functional RNAs or foreign proteins. Foreign proteins will typically encode proteins that may be foreign to plant hosts. Such foreign proteins will include, for example, enzymes for primary or secondary metabolism in plants, proteins that confer disease or herbicide resistance, commercially useful non-plant enzymes, and proteins with desired properties useful in animal feed or human food. Additionally, foreign proteins encoded by the transgenes will include seed storage proteins with improved nutritional properties, such as the high-sulfur 10 kD corn seed protein or high-sulfur zein proteins. Additional examples of a transgene suitable for use in the present invention include genes for disease resistance (e.g., gene for endotoxin of *Bacillus thuringiensis*, WO 92/20802)), herbicide resistance (mutant acetolactate synthase gene, WO 92/08794)), seed storage protein (e.g., glutelin gene, WO 93/18643)), fatty acid synthesis (e.g., acyl-ACP thioesterase gene, WO 92/20236)), cell wall hydrolysis (e.g., polygalacturonase gene (D. Grierson et al., *Nucl. Acids Res.*, vol. 14, p. 8595, 1986)), anthocyanin biosynthesis (e.g., chalcone synthase gene (H. J. Reif et al., *Mol. Gen. Genet.*, vol. 199, p. 208, 1985)), ethylene biosynthesis (e.g., ACC oxidase gene (A. Slater et al., *Plant Mol. Biol.*, vol. 5, p. 137, 1985)), active oxygen-scavenging system (e.g., glutathione reductase gene (S. Greer & R. N. Perham, *Biochemistry*, vol. 25, p. 2736, 1986)), and lignin biosynthesis (e.g. phenylalanine ammonia-lyase gene, cinnamyl alcohol dehydrogenase gene, o-methyltransferase gene, cinnamate 4-hydroxylase gene, 4-coumarate-CoA ligase gene, cinnamoyl CoA reductase gene (A. M. Boudet et al., *New Phytol.*, vol. 129, p. 203, 1995)).

Transgenes may function as transformation markers. Transformation markers include selectable genes, such as antibiotic or herbicide resistance genes, which are used to select transformed cells in tissue culture, non-destructive screenable reporters, such as green fluorescent and luciferase genes, or a morphological marker, such as "shooty", "rooty", or "tumorous" phenotype.

Additionally transgenes may encode proteins that affect plant morphology and thus may also be used as markers. Morphological transformation marker genes include cytokinin biosynthetic genes, such as the bacterial gene encoding isopentenyl transferase (IPT). IPT gene was proposed as a marker for transformation by Ebumina et al. (1997) *Proc. Natl. Acad. Sci. USA* 94:2117–2121), and Kunkel et al. *Nat. Biotechnol.* (1999), 17(9), 916–919. In the former case, the IPT gene was inserted inside a transposable element, whose excision following transformation resulted in the loss of the transposable element and the IPT gene. However, this method is inefficient (see Kunkel, supra), especially because of its low frequency of loss (1% or less). Kunkel, supra) proposed the use of an inducible IPT gene. However, this is also undesirable, since the bacterial IPT gene is not lost following transformation and that could be of concern from a regulatory point of view. Furthermore, it does not allow its use for retransformation for trait stacking. Thus, there is a need for an efficient regulated removal of morphological markers. Other morphological markers include developmental genes that can induce ectopic shoots, such as *Arabidopsis* STM, KNAT 1, or AINTEGUMANTA, Lec 1, *Brassica* "Babyboom" gene, rice OSH1 gene, or maize Knotted (Kn1) genes. Yet other morphological markers are the wild type T-DNA of Ti and Ri plasmids of *Agrobacterium* that induce tumors or hairy roots, respectively, or their constituent T-DNA genes for distinct morphological phenotypes, such as shooty (e.g., cytokinin biosynthesis gene) or rooty phenotype (e.g. rol C gene). Use of a morphological transformation marker to identify transformed tissue/organ and its subsequent removal (leaving behind the transgene of interest) restores normal morphology and development to transgenic tissues. This is especially useful for in planta transformation, where the morphological marker is used to obtain abnormal transgenic organs that are then corrected by site-specific recombination to form morphologically and developmentally normal transgenic plants without going through the time and labor intensive tissue culture methods for transformation.

Plant Hosts

The present invention additionally provides plant hosts for transformation with the present constructs. Moreover, the host plant for use in the present invention is not particularly limited. Examples of herbaceous plant used as the host plant include tobacco (*Tabacum*), tomato (*Lycopersicom*), sweet potato (*Impoea*), potato (*Solanum*), carrot (*Dacus*), lettuce (*Lactuca*), cauliflower (*Brassica*), cabbage (*Brassica*), oilseed rape (*Brassica*), sunflower (*Helianthus*), sugar best (*Bela*), asparagus (*Asparagus*), banana (*Musa*), cotton (*Gossypium*), arabidopsis (*Arabidopsis*), alfalfa (*Medicago*), peas (*Pisum*), soybean (*Glycine*), rice (*Oryza*), corn (*Zea*), and rye (*Secale*). Examples of arboreous plant used as the host plant include poplar (*Populus*), eucalypti (*Eucalyptus*), acacia (*Acacia*), pear (*Pyrus*), apple (*Malus*), grape (*Vitis*), walnut (*Juglans*), plum (*Prunus*), rose (*Rosa*), and spruce (*Picea*). However, the host plants for use in the present invention are not limited thereto.

Plant Transformation

One skilled in the art recognizes that the expression level and regulation of a transgene in a plant can vary significantly from line to line. Thus, one has to test several lines to find one with the desired expression level and regulation. Once a line is identified with the desired regulation specificity of a chimeric Cre transgene, it can be crossed with lines carrying different inactive replicons or inactive transgene for activation.

A variety of techniques are available and known to those skilled in the art for introduction of constructs into a plant cell host. These techniques include transformation with DNA employing *A. tumefaciens* or *A. rhizogenes* as the transforming agent, electroporation, particle acceleration, etc. (See for example, EP 295959 and EP 138341). It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciotti et al. (1985) *Bio/Technology* 3:241; Byrne et al. (1987) *Plant Cell, Tissue and Organ Culture* 8:3; Sukhapinda et al. (1987) *Plant Mol. Biol.* 8:209–216; Lorz et al. (1985) *Mol. Gen. Genet.* 199:178; Potrykus (1985) *Mol. Gen. Genet.* 199:183; Park et al., *J. Plant Biol.* (1995), 38(4), 365–71; Hiei et al., *Plant J.* (1994), 6:271–282). The use of T-DNA to transform plant cells has received extensive study and is amply described (EP 120516; Hoekema. In: *The Binary Plant Vector System*, Offset-drukkerij Kanters B. V.; Alblasserdam (1985), Chapter V, Knauf, et al., *Genetic Analysis of Host Range Expression by Agrobacterium* In: *Molecular Genetics of the Bacteria-Plant Interaction*, Puhler, A. ed., Springer-Verlag, New York, 1983, p. 245; and An, et al., *EMBO J.* (1985)

4:277–284). For introduction into plants, the chimeric genes of the invention can be inserted into binary vectors as described in the examples.

Other transformation methods are available to those skilled in the art, such as direct uptake of foreign DNA constructs (see EP 295959), techniques of electroporation (see Fromm et al. (1986) *Nature* (London) 319:791) or high-velocity ballistic bombardment with metal particles coated with the nucleic acid constructs (see Kline et al. (1987) *Nature* (London) 327:70, and see U.S. Pat. No. 4,945,050). Once transformed, the cells can be regenerated by those skilled in the art. Of particular relevance are the recently described methods to transform foreign genes into commercially important crops, such as rapeseed (see De Block et al. (1989) *Plant Physiol.* 91:694–701), sunflower (Everett et al. (1987) *Bio/Technology* 5:1201), soybean (McCabe et al. (1988) *Bio/Technology* 6:923; Hinchee et al. (1988) *Bio/Technology*, 6:915; Chee et al. (1989) *Plant Physiol.* 91:1212–1218; Christou et al. (1989) *Proc. Natl. Acad. Sci USA* 86:7500–7504; EP 301749), rice (Hiei et al., *Plant J.* (1994), 6:271–282), and corn (Gordon-Kamm et al. (1990) *Plant Cell* 2:603–618; Fromm et al. (1990) Biotechnology 8:833–839).

Transgenic plant cells are then placed in an appropriate selective medium for selection of transgenic cells which are then grown to callus. Shoots are grown from callus and plantlets generated from the shoot by growing in rooting medium. The various constructs normally will be joined to a marker for selection in plant cells. Conveniently, the marker may be resistance to a biocide (particularly an antibiotic such as kanamycin. G418 bleomycin, hygromycin, chloramphenicol, herbicide, or the like). The particular marker used will allow for selection of transformed cells as compared to cells lacking the DNA which has been introduced. Components of DNA constructs including transcription cassettes of this invention may be prepared from sequences which are native (endogenous) or foreign (exogenous) to the host. By "foreign" it is meant that the sequence is not found in the wild-type host into which the construct is introduced. Heterologous constructs will contain at least one region which is not native to the gene from which the transcription-initiation-region is derived.

To confirm the presence of the transgenes in transgenic cells and plants, a Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

DESCRIPTION OF THE PREFERRED EMBODIMENTS

The present invention solves the problem of the conditional expression of various genetic traits in plants during specific times in a plant life cycle, in specific plant tissues, or in a specific generation by tying the expression of these traits to regulated promoters will additionally timing expression through the judicious use of site-specific recombinase systems. The constructs of the invention are referred to as recombinase elements. Each recombinase element will comprise at least one plant promoter. The promoters may be constitutive, inducible, tissue specific or developmental stage-specific promoters. Combinations of developmentally-regulated germline promoters are particularly useful. One recombinase element will typically consist of a single promoter operably linked to a recombinase. Second, third and fourth recombinase elements may consist of different promoters that will either drive the expression of a second or third recombinase or the expression of a transgene. Transgenes of the present invention will encode genetic traits, or various transformation or morphological markers. By configuring the recombinase elements and placing them in different parental plants it is possible to have the transgene expressed in specific tissues or during specific times in a plant life cycle or in a specific generation and then, if desirable, have the transgene selectively excised when no longer convenient. It will be appreciated that any number of recombinase elements may be combined with these essential components to effect the regulate expression and expression of transgenes.

The invention provides constructs and methods for the conditional or regulated expression or excision of a transgene in a plant system. In its most basic form this may be accomplished through the use of a single site-specific recombinase system and a pair of regulated promoters. Such as scheme is illustrated in FIG. 1. Referring to FIG. 1, a first recombinase element comprising a promoter (P1) operably linked to a recombinase (R1) coding sequence, is provided. Similarly a second recombinase element comprising a second, different promoter (P2) placed upstream of a stop fragment (STP) which in turn is upstream of a transgene (TG) encoding a trait. The stop fragment (STP) is bounded by site specific sequences responsive to the recombinase, or recombinase sequences (RS1). Typically the first and second recombinase elements are provided in different plants, although it will be appreciated that, in the case of an inducible P1 promoter, a single plant may be co-transformed with both elements. After crossing, or co-transformation, where the first and second recombinase elements are present in the same tissue, activation of the first promoter (P1) results in expression of the recombinase (R1) which in turn excises the stop fragment (STP) from the second recombinase element. Activation of the second promoter effects expression of the transgene (TG) encoding a trait. One utility of such a scheme is to activate a transgene, whose expression is detrimental to normal plant development, only in the first generation. Such transgenes include those that result in too high levels of a desired product to be phytotoxic are not expressed during breeding but only in the harvestable generation.

Figure 2:
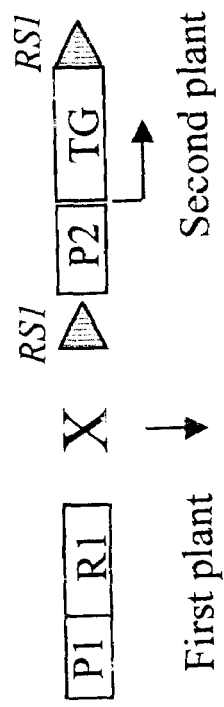
FIG. 2 illustrates a scheme for the use of a single site-specific recombinase system for the regulated excision of a transgene in a first generation plant.
Figure 2:
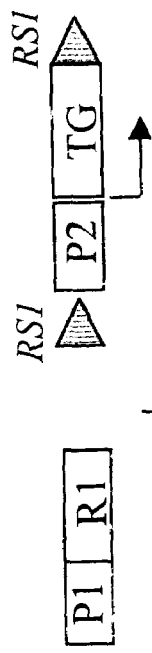
Figure 2:
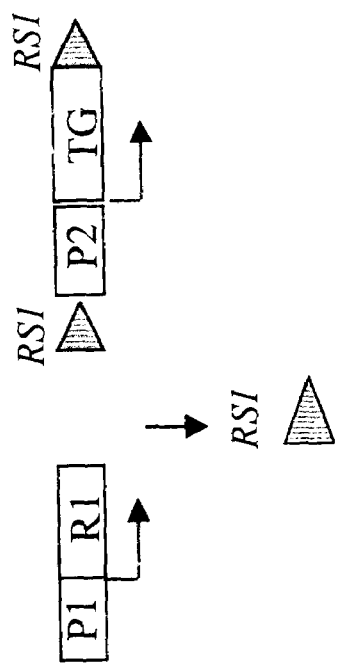

In an alternate embodiment the invention provides a constructs and methods for removal or excision of the transgene encoding a trait at some specified developmental stage in a plant life cycle of the first or the second generation. A simple example of this method is illustrated in FIG. 2. Referring to FIG. 2, again two recombinase elements are provided. The first recombinase element comprises a germline promoter (P1) operably linked to a recombinase coding sequence (R1). The second recombinase element comprises a promoter (P2) operably linked to a transgene (TG) encoding a trait where the entire recombinase element is bounded by recombinase sequences (RS1) responsive to the recombinase. Typically the first recombinase element is provided in a first plant whereas the second recombinase element is provided in a second plant although it will be appreciated that, in the case of an inducible P1 promoter, a single plant may be co-transformed with both elements. Where P1 is a developmentally regulated germline promoter, a cross of the first and second plants results in activation of P1 and the expression of recombinase (R1) in the first generation. When TG is expressed in vegetative tissues and where P1 is a common or male germline promoter that is activated late in the plant life cycle to express the recombinase (R1) and cause the excision of the P2-TG chimeric element in the first generation from the seed or pollen, respectively. One utility of this scheme is to remove a transgene from pollen to prevent its environmental impact, escape to wild type relatives, and escape to neighbor crops. Another utility is to remove the trait gene from progeny seeds to prevent residual or volunteer plants in the next growing season, reduce regulatory concerns, and provide a tighter control on unwanted gene flow.

Yet another utility is for marker excision. i.e., removal of transformation marker for easier regulatory approval and for reusing the marker for retransformation. Antibiotic or herbicide resistance genes are used as selectable markers in plant transformation to select for the rare transgenic cells from nontransgenic ones. However, the presence of such markers in transgenic plants is undesirable because of regulatory concerns/requirements as well as because it prevents recurrent use of the selectable marker for stacking trait transgenes. The use of a bacterial IPT gene as a marker for transformation was proposed by Ebumina et al. (1997) *Proc. Natl. Acad. Sci. USA* 94:2117–2121') and and Kunkel et al. *Nat. Biotechnol.* (1999), 17(9), 916–919. In the former case, the IPT gene was inserted inside a transposable element, whose random excision following transformation resulted in the loss of the transposable element and the IPT gene. However, this method is inefficient (see Kunkel, supra), especially because of its low frequency of loss (1% or less). Kunkel, supra) proposed the use of a chemically-inducible IPT gene. However, this is also undesirable, since the bacterial IPT gene is not lost following transformation and that could be of concern from a regulatory point of view. Furthermore, it does not allow its use for retransformation for trait stacking. Therefore, there is a need for an efficient, regulatable excision of a constitutively expressed transformation marker gene. We propose inserting a transformation marker gene within site-specific sequences such that it is efficiently excised upon the expression of a chimeric recombinase gene under the control of a regulated or an inducible promoter following transformation. SAM-specific genes could be particularly useful in that their promoters could express Cre and cause SSR in shoot apices following transformation of undifferentiated cells/calli. This would be useful to remove the selectable genes early in tissue-culture but after the selection. This can be tested with a non-destructive excision reporter such as GFP or luciferase either in *agrobacterium*-mediated transformation of tobacco (leaf-disc method) or *Arabidopsis*, or by biolistic bombardment in soybean or corn embryogenic cultures. The said invention provides for such promoters (AP3, BCP1, HSP18.2)

In a particularly useful embodiment, the invention may be used for in planta transformation to circumvent the need to go through time-consuming and laborious plant tissue culture method of transformation. This relies on the use of a scorable (non-selectable) marker transgene that induces morphological or visible changes in transgenic tissue (such as shoots and/or roots. Examples of such genes are STM, KNAT 1 homoebox genes, Lec 1, or ANT gene, or even *agrobacterium* T-DNA that can induce proliferation and redifferentiation in planta. Subsequent loss of these markers from the germline under the control of a regulated site-specific recombinase (as above) will allow recovery of morphologically normal transformants on the plant. The regulated recombinase gene can either be within the site-specific sequences or outside. The promoter for the recombinase gene can be from a developmentally regulated germline specific gene, such as those involved in meristem identity, organ primordia, or anther/pistil. It can also be inducible by a chemical, such as a safener (e.g., IN2 promoter) or by heat shock, such as *Arabidopsis* HSP18.2 gene. The said invention provides for such promoters (AP3, BCP1, HSP).

In other preferred embodiments the invention will make use of two or more developmentally staggered site-specific recombinations systems. Although SSRs have been used singly as genetic switches, two (or more) SSRs under the control of different constitutive or regulated promoters can be used as a series of genetic switches within a plant's life cycle, such that conditional expression of one recombinase (R1) at one stage activates another recombinase (R2) at a later stage. Thus, one can conditionally trigger the process at a convenient developmental stage, such as germination, but get delayed effects at later stages.

Conditionality to the first SSR is provided by either chemical application or a genetic cross that combines its recombinase gene with its cognate target gene/s. The latter is more amenable for hybrid crops. Chemical application on seeds or during germination is likely to overcome the chemical's cost and problem with its biokinetics into target cells. Chemical application can also be done in the prior generation by using a relay of three, rather than two, site-specific recombination systems. Thus, the chemical can be applied to germinating seeds in the last generation of seed production to induce one type of SSR that results in another type, say in late seed development of progeny seeds, that, in turn, results in a third type of SSR to express in early seeds to remove the trait gene. In another embodiment R1 can be chemically repressible, such that the application of the chemical represses SSR I (R1) to allow production of seeds with the transgenic trait. Here, in the absence of the chemical, such as in the farmers' field, the crop is genetically triggered to enable trait gene expression and/or its subsequent removal on cue.

Such combinations of two or more different site-specific recombinations, whether linked or unlinked, provide novel and useful tools to control transgene expression and/or removal in the first, second, or third generations that are not currently available in agricultural biotechnology. Thus, a pair of developmentally staggered SSRs may be used as ON—ON or ON-OFF (transgene removal) switches. The salient feature in both schemes, is that expression of R2 and/or trait genes does not have to occur immediately upon enablement (i.e., removal of the stop fragment) by R1 but are rather controlled solely by the choices of P2 and P3 promoters. While the following embodiments involve two site-specific recombinations, it is recognized that the strategy can be extended to include addition site-specific recombinations for controlling transgene expression even beyond the second generation or to include more elaborate transgene activation or removal.

Figure 3:
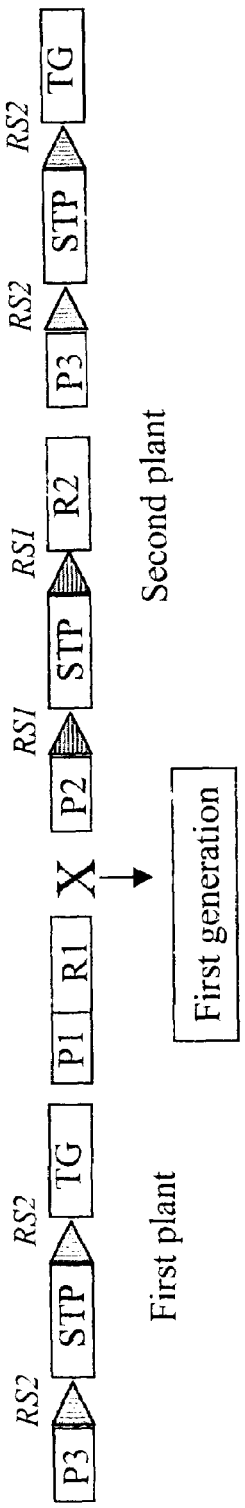
FIG. 3 illustrates a scheme for the use of a dual site-specific recombinase system for the conditional expression of a transgene in a second generation plant.
Figure 3:
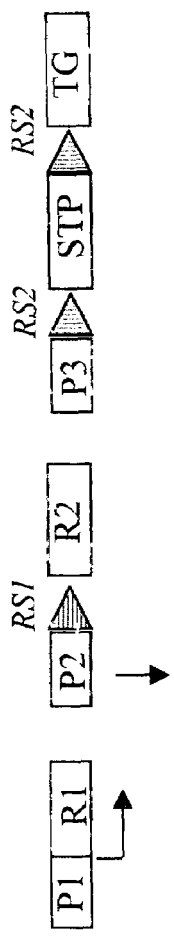
Figure 3:
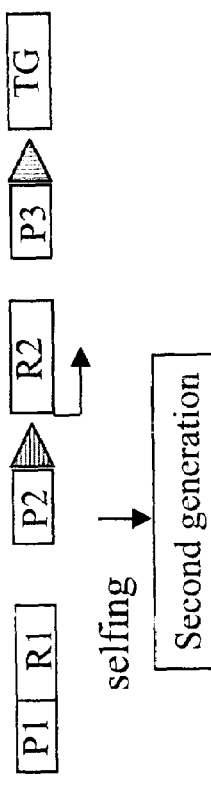
Figure 3:
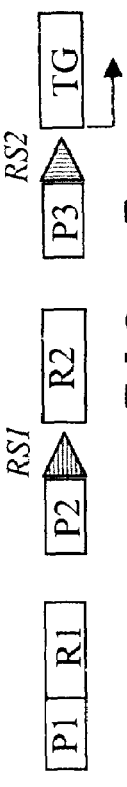

In one embodiment, two SSRs may be staggered as ON—ON switches to get trait expression later than possible with only one SSR. One such utility is for allowing trait expression only in the second generation. This is important when trait expression is detrimental to normal plant development, such as seed germination or seedling growth, and it is undesirable for trait expression during breeding or in the farmer's field but desirable in the generation that is harvested and processed. Thus, in an alternate preferred embodiment the invention will make use of at least three separate recombinase elements as shown in FIG. 3. Referring to FIG. 3, a first recombinase element is provided consisting of a first promoter (P1) operably linked to a first recombinase coding sequence (R1). A second recombinase element is provided consisting of a second different promoter (P2) upstream of a stop fragment (STP) which is in turn upstream of a second recombinase coding sequence (R2), where the stop fragment (STP) is bounded by recombinase sequences responsive to the first recombinase (RS2). A third recombinase element is provided consisting of a third promoter (P3) upstream of a stop fragment (STP) which is in turn upstream of a trait transgene (TG), where the stop fragment (STP) is bounded by recombinase sequences (RS2) that are responsive to the second recombinase. It will be appreciated that, when P1 is an inducible promoter, the first, second and third recombinase elements may be combined into a plant through any means including crossing, or co-transformation and when P1 is not an inducible promoter, the first and the second elements are brought together in the first generation by a cross. In one particularly useful embodiment a first plant is provided having the first and third recombinase elements while a second plant is provided having the second and third recombinase elements. Crossing the first and second plant will give rise to the first generation plant in which the first recombinase is expressed excising the stop fragment (STP) from the second recombinase element and allowing the expression of recombinase R2 under the control of P2 promoter, which recombinase, in turn, excises the stop fragment from the third recombinase element, allowing expression of the trait gene under the control of P3 promoter in the second and subsequent generations. Here P1, P2, and P3 promoters are not all activated simultaneously. They may each be activated at a different stage: first P1 in first generation, then P2 in first or second generation, and last P3 in the second generation; alternatively, P1 and P2 are activated together in the first generation and P3 in the second generation; alternatively, P1 is activated in the first generation and P2 and P3 are activated together in second generation. Also promoters for expression in first generation express in common germline, while promoters P3 and P2, when it occurs in second generation, may be in second generation germline or somatic cells and may be developmental stage-specific or chemically inducible. One utility of this scheme is to express traits, such as developmental traits, only in second and subsequent generation. Such developmental traits include apomixes, parthenocarpy, flowering (Nilsson et al. (1998) *The Plant Journal* 15:799–804), self-incompatibity (Stone et al. (1999) *Science* 286:1729), altered flowering time (Mandel and Yanofsky *Nature* (1995) 377:522; Weigel and Nilsson (1995) *Nature* 377:495), type of pollination (selfing vs. crossing), and barriers to cross pollination, pollination control, self-incompatibility, sterility, etc. Some of these traits will require expression of a trait transgene encoded polypeptide, such as a toxin or a transcriptional factor that regulates endogenous genes, others will not, such as when a trait transgene co-suppresses or silences an endogenous gene (see Chuang C F, Meyerowitz E M (2000) *Specific and heritable genetic interference by double-stranded RNA in Arabidopsis thaliana. Proc Natl Acad Sci USA.* 97:4985–4990).

Another utility of this application is to allow trait gene expression in germinating seeds or seedlings of the second generation after harvest in contained bioreactors. This is important when trait expression of toxic material is undesirable in the field. In an extension of this concept, another transgene is activated that results in trait gene removal in the second generation or the second generation has a lethal gene that block development or a sterility gene that prevents flowering and seed set to further genetically contain the trait gene.

In another embodiment of the invention two or more site-specific recombination may allow conditional and transient transgene expression by linking trait activation and trait removal.

Figure 5:
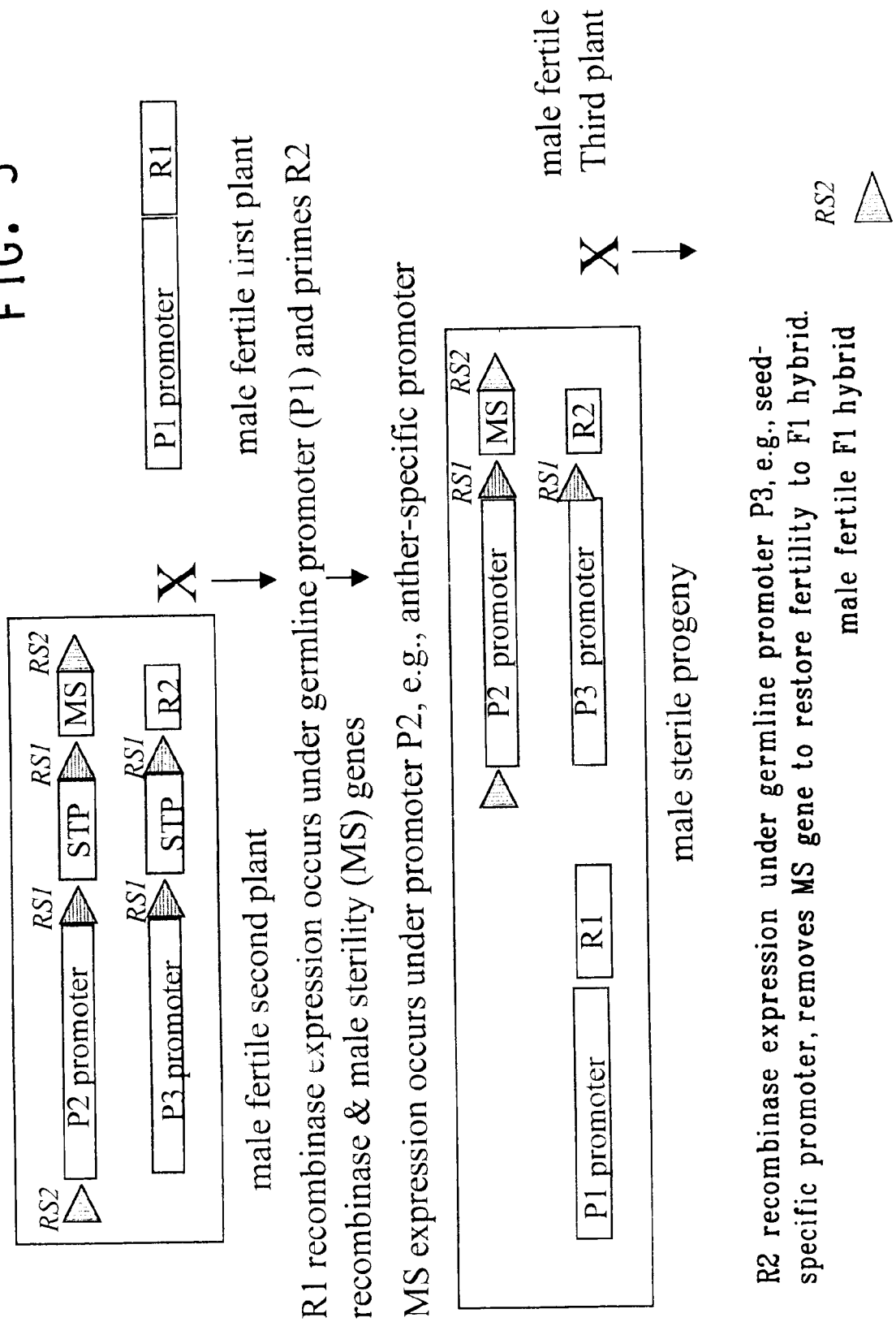
FIG. 5 illustrates a scheme for the use of a dual site-specific recombinase system to effect conditional male sterility in a first generation plant.
Figure 6:
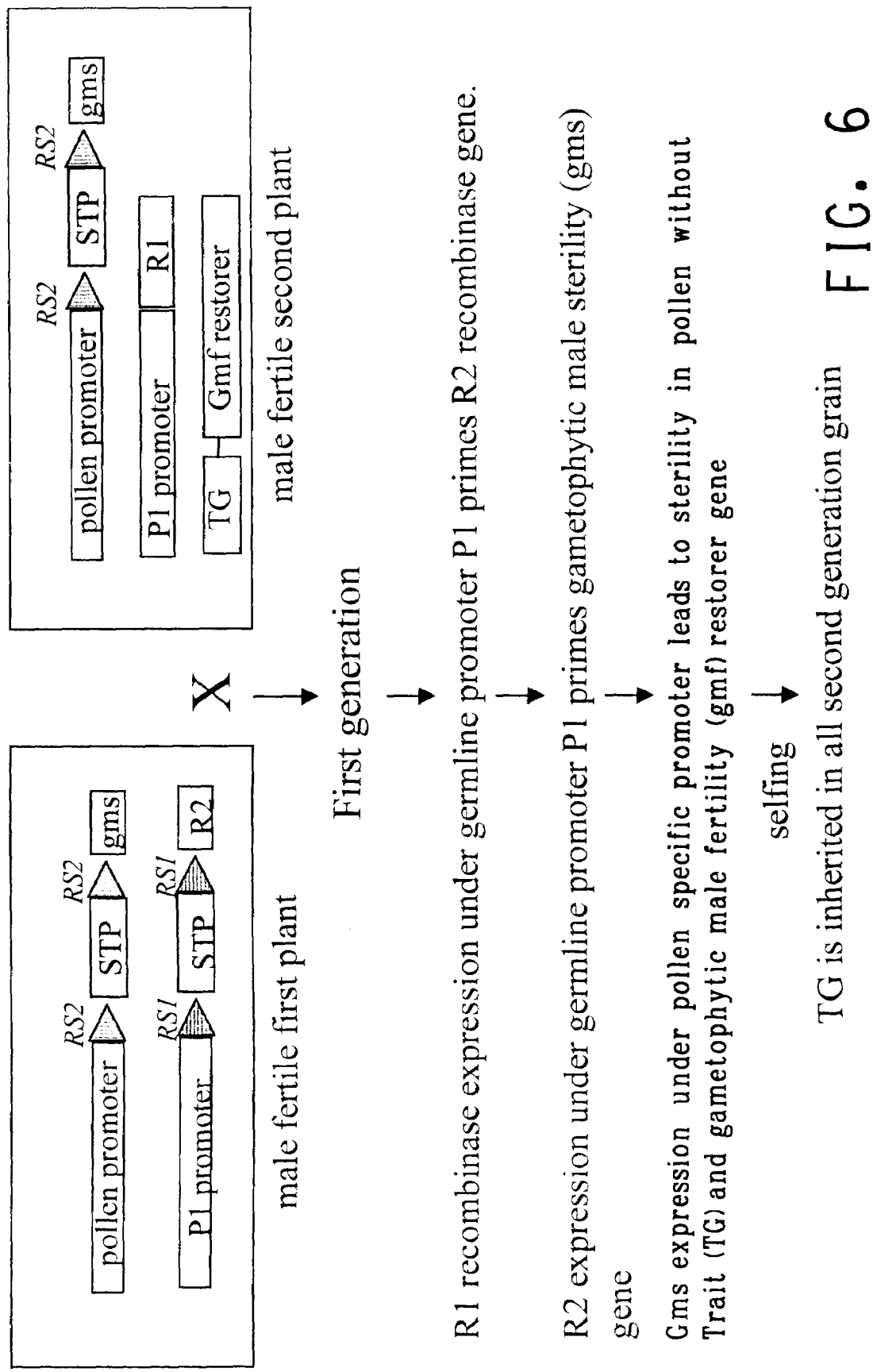
FIG. 6 illustrates a scheme for the use of a dual site-specific recombinase system to effect conditional gametophytic male sterility in a second generation plant.
Figure 8:
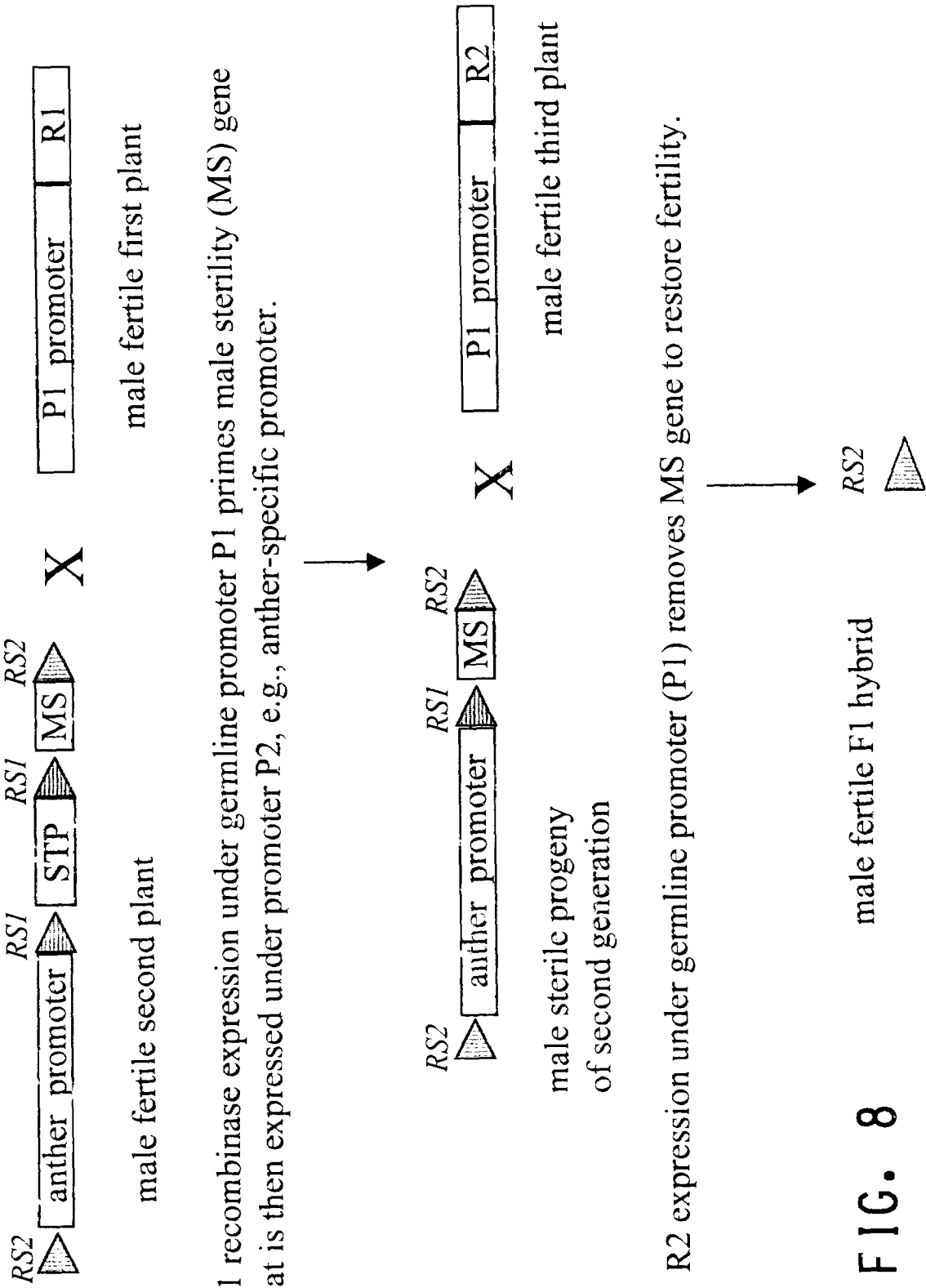
FIG. 8 illustrates a scheme for the use of a dual site-specific recombinase system to effect conditional male sterility for hybrid seeds.

Here two SSRs may be developmentally staggered, such that R2 recombinase removes a transgene. This will result in an ON-OFF (by transgene removal) switch to get transient trait expression. Trait gene removal may be unlinked (FIGS. 2, 8) or linked (FIGS. 4,5,6) to trait gene expression. The latter provides a more stringent control of trait gene expression. These Figures show that only the trait gene is removed, although all transgenes could be removed by having them flanked by appropriate recombinase sites.

Figure 4:
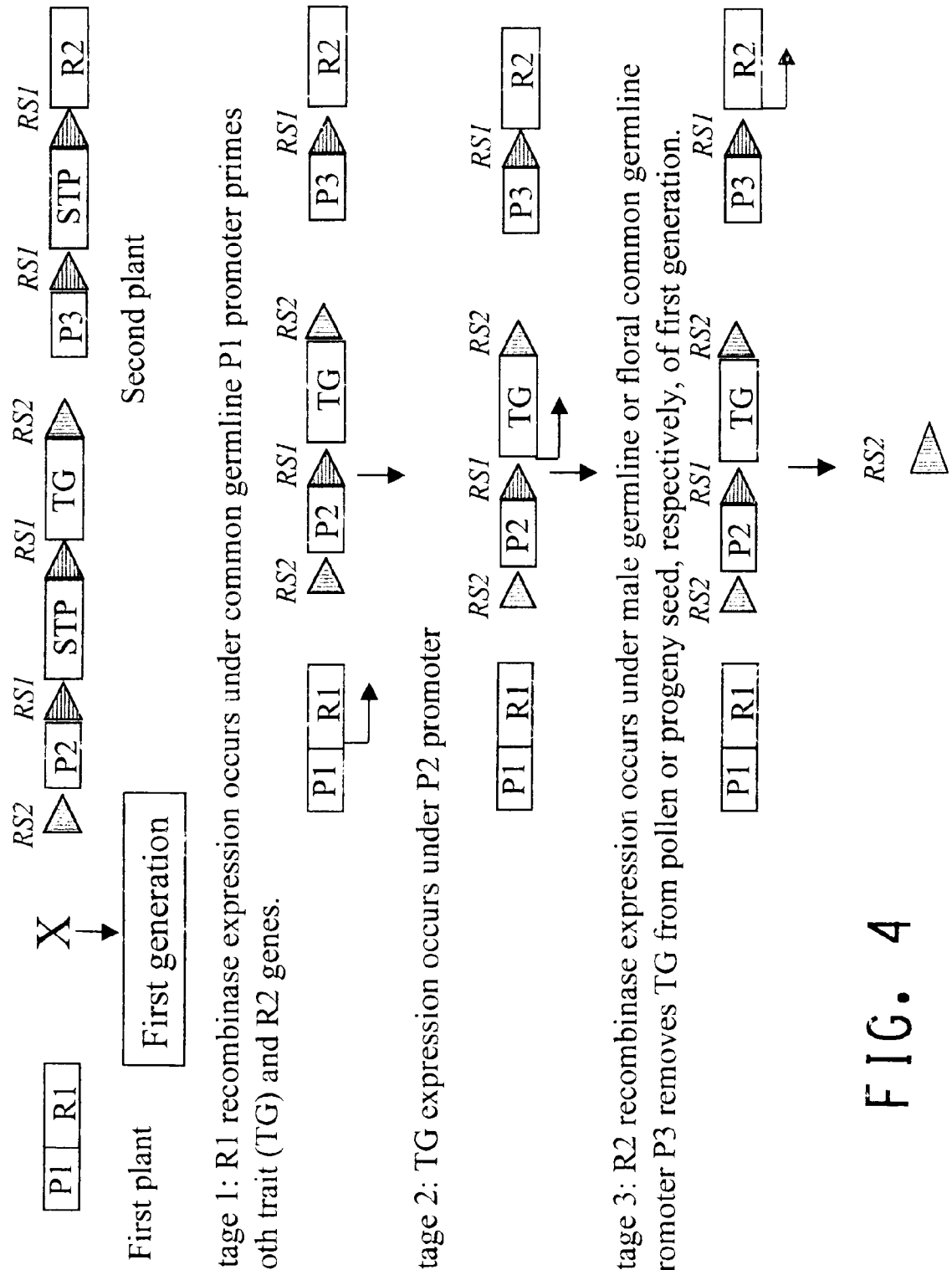
FIG. 4 illustrates a scheme for the use of a dual site-specific recombinase system for the conditional expression of a transgene in a first generation plant and it's subsequent removal.

For example, in some situations it may be desirable to express a trait at one point in a plant life cycle, but then have that trait removed in a later generation. Such a scheme is illustrated in FIG. 4. Referring to FIG. 4, two plants are provided. The first plant will contain a first recombinase element comprising a first promoter (P1) operably linked to a first recombinase coding sequence (R1). The second plant will contain both second and third recombinase elements. The second element will consist of a second promoter (P2) upstream of a stop fragment (STP) which in turn is upstream of a transgene encoding a trait (TG). The entire second recombinase element is flanked by recombinase sequences responsive to a second recombinase (RS2). The third recombinase element is comprised of a third promoter (P3) upstream of a stop fragment (STP) which is in turn upstream of a second (different from R1) recombinase coding sequence (R2). In both the second and third recombinase elements the stop fragments (STP) are flanked by recombinase sequences responsive to the first recombinase (RS1).

It will be appreciated that, when P1 is an inducible promoter, the first, second and third recombinase elements may be combined into a plant through any means including crossing, or co-transformation and when P1 is not an inducible promoter, the first and the second elements are brought together in the first generation by a cross. Thus, where the first promoter (P1) is a developmentally regulated germline promoter, crossing the first and second plants will result in the activation of P1 and the expression of the first recombinase (R1). Expression of the first recombinase (R1) primes both the second and third recombinase elements by excising the stop fragment (STP) in each. Where the second promoter (P2) is activated prior to the third promoter (P3), the transgene is expressed. The third promoter (P3) is a common or male germline promoter, whose activation will cause the expression of R2 and the removal of the trait gene from the progeny seed of the second generation or pollen of the first generation. Thus, the invention provides for both conditional expression of the trait and its subsequent excision when no longer useful.

Here P1, P2, and P3 promoters are not all activated simultaneously and P3 promoter is always activated after useful expression of the trait gene under P2 promoter. Promoter P1 is activated in the germline of first generation, P2 promoter is activated in germline or somatic cells of the first or second generation, and P3 promoter is activated in the common or male germline of the first or second generation following useful trait expression under P2. The three promoters may each be activated at different developmental stages; for example, promoter P1 is activated first in the common germline of first generation, then P2 in somatic or somatic plus germline cells of first or second generation, and last P3 in the common or male germline cells of first or second generation following useful trait expression; alternatively, P1 and P2 may be activated together in the first generation and P3 later in the first generation or in the second generation; or P1 may be activated first in the common germline of the first generation and P2 in somatic cells and P3 in germline cells of first or second generation. This scheme combines two utilities: first, trait genes can be activated and expressed only in the desired generation, especially useful when the target product is phytotoxic; and second, after trait genes have served their usefulness, they are removed from pollen or seeds for better genetic containment and prevention of unwanted gene flow.

Other utilities include molecular approaches for controlling developmental traits, such as flowering (Nilsson et al. (1998) *The Plant Journal* 15:799–804'), self-incompatibility (Stone et al. (1999) *Science* 286:1729), altered flowering time (Mandel and Yanofsky *Nature* (1995) 377:522; Weigel and Nilsson (1995) *Nature* 377:495), apomixes, parthenocarpy, type of pollination (selfing vs. crossing), and barriers to cross pollination, etc.

One particularly useful trait is conditional male sterility, which is important for hybrid seed production. The present invention is particularly useful for controlling male sterility by providing a simple molecular biology approach for conditional male sterility. Male sterility can be sporophtytic or gametophytic. For example, Referring to FIG. 5, two male fertile plants are provided. The first plant contains a first recombinase element consisting of a first promoter (P1) operably linked to a first recombinase coding sequence (R1). The second plant contains both a second and third recombinase element. The second element will consist of a second promoter (P2) upstream of a stop fragment (STP) which in turn is upstream of a transgene encoding the male sterile trait (MS). The entire second recombinase element is flanked by recombinase sequences responsive to a second recombinase (RS2). The third recombinase element is comprised of a third promoter (P3) upstream of a stop fragment (STP) which is in turn upstream of a second recombinase coding sequence (R2). In both the second and third recombinase elements the stop fragments (STP) are flanked by recombinase sequences responsive to the first recombinase (RS1).

It will be appreciated that, when P1 is an inducible promoter, the first, second and third recombinase elements may be combined into a plant through any means including crossing, or co-transformation and when P1 is not an inducible promoter, the first and the second elements are brought together in the first generation by a cross. Thus, where the first promoter (P1) is a constitutive or developmentally regulated common germline promoter, crossing the first and second plants results in expression of the first recombinase (R1) and the priming of both the second and third recombinase elements by removal of the stop fragments (STP). Where the second promoter (P2) is anther specific the male sterile gene is expressed in the sporophyte cells of the anther to render the first generation male sterile. Where the third promoter (P3) is a seed specific promoter, the male sterility transgene is excised in the F1 hybrid seed to render it male fertile.

The dominant male sterility gene can encode a toxin (e.g., barnase, avidin, RIP) gene or a co-suppressor of a fertility gene (e.g., corn MS45 gene). This element can also be a constitutive promoter expressing a co-suppressor of an anther-specific fertility gene (e.g., corn MS45 gene).

Figure 7:
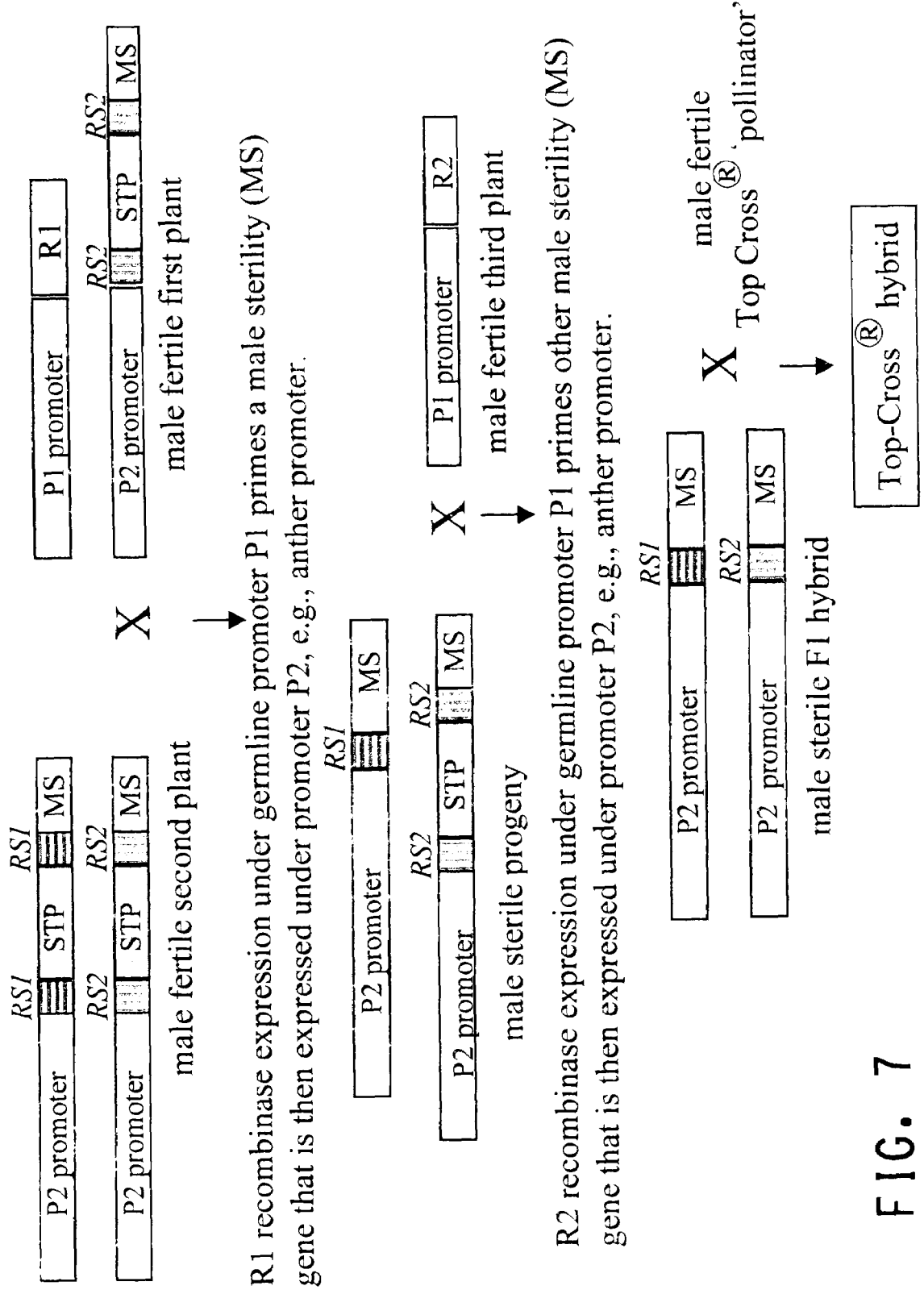
FIG. 7 illustrates a scheme for the use of a dual site-specific recombinase system to effect conditional male sterility in a Top Cross (R second generation.

The present invention may be specifically applied for the conditional control of male sterility in corn according to the TopCross® method of breeding. When male sterility is required even in the next generation, such as in corn Top-Cross® the above scheme can be modified to omit fertility restoration and incorporate a second conditional male sterility system. For example, referring to FIG. 7, two male fertile plants are provided. The first plant comprises a first and third recombinase element while the second plant comprises a second and third element. The first recombinase element comprises a first promoter (P1) operably linked to a first recombinase coding sequence (R1). The second recombinase element comprises a second promoter (P2) upstream of a stop fragment (STP) which is in turn upstream of a transgene encoding male sterility (MS), wherein the stop fragment (STP) is bounded by site-specific recombinase sequences responsive to the first recombinase (RS1). The third recombinase element comprises a second promoter (P2) upstream of stop fragment (STP), which is in turn upstream of a transgene encoding male sterility (MS) wherein the stop fragment (STP) is bounded by site-specific recombinase sequences responsive to the second (and different from R1) recombinase (RS2). A third male fertile plant is also provided having a fourth recombinase element comprising a first promoter (P1) operably linked to a second recombinase coding sequence (R2)

A cross of the first and second plants produces a first generation plant. Where the first promoter is constitutive or germline specific P1 is activated and R1 is expressed. The expression of R1 excises the stop fragment (STP) from the second recombinase element. Where P2 is activated in the first generation the MS transgene is expressed resulting in a male sterile plant. Crossing the male sterile plant with the third plant produces an F1 hybrid sterile plant. The plant is sterile since, where P1 is activated in the hybrid, R2 is expressed causing the excision of stop fragment (STP) from the third recombinase element, allowing the expression of the second MS gene, where P2 is activated. Crossing this male sterile F1 hybrid with a TopCross® pollinator results then in a TopCross® hybrid.

The methods of the present invention may also be applied to provide conditional male sterility in seeds. For example, referring to FIG. 8, three plants are provided. The first plant comprises a first recombinase element, the second comprises a second recombinase element and the third comprises a third element. The first element comprises a first promoter (P1) operably linked to a first recombinase coding sequence (R1). The second element comprises an anther promoter upstream of a stop fragment (STP) which is in turn upstream of a male sterility encoding gene (MS). The stop fragment (STP) is bounded by site-specific recombinase sequences responsive to the first recombinase (RS1) and the entire element is bounded by site-specific recombinase sequences responsive to a second recombinase (RS2). The third element comprises the first promoter (P1) operably linked to a second recombinase coding sequence (R2).

It will be appreciated that, when P1 is an inducible promoter, the first and second recombinase elements may be combined into a plant through any means including crossing, or co-transformation. Where P1 is constitutive or developmentally regulated common germline promoter, crossing the first and second plants results in a first generation plant where R1 is expressed and the stop fragment is excised from the second recombinase element. Where the anther promoter is activated the male sterility transgene (MS) is expressed and the plant is male sterile. Crossing this male sterile plant with the third plant results in the removal of the MS gene and restoration of fertility in subsequent generations.

The present invention will also allow for the conditional control of gametophytic male sterility to ensure that a trait transgene that is present in a heterozygous state in one of two parent lines of a cross is expressed in all second generation (F2) grain. For example, referring to FIG. 6, two male fertile plants are provided. The first plant comprises second and third recombinase elements. The second plant comprises first and third recombinase elements and a transgene physically linked to a gametophytic male fertility restorer gene. The first recombinase element comprises a first promoter (P1) operably linked to a first recombinase coding sequence (R1). The second recombinase element comprises a first promoter (P1) upstream of a stop fragment (STP) which is in turn upstream of second recombinase coding sequence (R2), wherein the stop fragment (STP) is bounded by site-specific recombinase sequences responsive to the first recombinase (RS1). The third recombinase element comprises a pollen specific promoter upstream of a stop fragment (STP) which is in turn upstream of a transgene encoding gametophytic male sterility (gms) coding sequence, wherein the stop fragment (STP) is bounded by site-specific recombinase sequences responsive to the second recombinase (RS2). The male sterility gene can encode barnase. The fourth element is linked trait gene (TG) and a gametophytic male fertility (gmf) restorer gene. The gmf restorer gene can be barstar, when the sterility gene is barnase.

When the first and second plants are crossed a first generation plant is produced. Where the first promoter (P1) is a constitutive or developmentally regulated common germline promoter; the first promoter is activated causing the expression of the first recombinase (R1). Expression of the R1 resulted in removal of the stop fragment (STP) from the second recombinase element and expression of the second recombinase (R2). Expression of R2 results in the removal of the stop fragment (STP) from the third recombinase element and the priming of that element for expression of the gametophytic male sterility (gms) gene under the control of a pollen promoter. This system allows for the expression of the gametophytic male sterility gene in pollen without the trait gene-gmf gene but not in pollen with the trait gene-gmf gene.

In order to accomplish the above metioned embodiments, this invention discloses the use of promoters for either male germline, floral common germline, and vegetative SAM common germline SSR. It also provides for an excision reporter construct that one skilled in the art can screen promoters with the desired activation specificities.

Site-specific recombinations in germline may be accomplished by the regulated expression of Cre using promoters from germline cell-specific genes promoters. These SSRs may be specific for male, female, or common germlines.

Examples of likely genes for germline promoters are:
a) AP3 and PI homeotic genes, and anther genes (SAP, Bcp1, etc) for male germline, or male gametophyte promoters, such as LAT52 (also see Twell et al. (1998) *Trends in Plant Sciences* 3:305)
b) Petunia's FBP7 and FBP11 involved in the formation of ovule primordium, *Arabidopsis* ANT and HLL genes involved in initiation of ovule protrusion for female germline; and
(i) shoot apical meristem (SAM) genes, organ primordia-specific genes, and floral homoetic genes, such as AG, LFY and ER for common germline. This category is especially useful for removing selectable genes early in tissue-culture following selection in tissue culture. Examples of such homoetic genes are: shoot apical meristem (SAM) genes include WUS and STM, maize KN1, rice OSH1, and UNUSUAL FLORAL ORGANS (UFO) gene.

It is also disclosed that the specificity of germline promoters can be the same as expected for the endogenous gene from which the promoter is derived or be changed depending on the transgenic line carrying the construct. Thus, AP3 was shown to confer vegetative SAM common germline, floral SAM common germline, and floral male germline excisions depending on the line. Such variation in transgene expression in not uncommon and one skilled in the art can screen and identify lines with the desired germline specificity.

EXAMPLES

The present invention is further defined in the following Examples. These Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and Enquist, L. W. Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Restriction enzyme digestions, phosphorylations, ligations and transformations were done as described in Sambrook, J. et al., supra. Restriction enzymes were obtained from New England Biolabs (Boston, Mass.), GIBCO/BRL (Gaithersburg, Md.), or Promega (Madison, Wis.). Taq polymerase was obtained from Perkin Elmer (Branchburg, N.J.). Growth media was obtained from GIBCO/BRL (Gaithersburg, Md.).

The *Agrobacterium tumefaciens* strain LBA4404 was obtained from Dr. R. Schilperoot, Leiden (Hoekema et al. *Nature* 303:179–180, (1983)).

Transformation Protocols

Biolistic transformations were done essentially as described in U.S. Pat. No. 4,945,050, hereby incorporated by reference. Briefly, gold particles (1 mm in diameter) are coated with DNA using the following technique. Ten ug of plasmid DNAs are added to 50 uL of a suspension of gold particles (60 ug per uL). Calcium chloride (50 uL of a 2.5 M solution) and spermidine free base (20 uL of a 1.0 M solution) are added to the particles. The suspension is vortexed during the addition of these solutions. After 10 min, the tubes are briefly centrifuged (5 sec at 15,000 rpm) and the supernatant removed. The particles are resuspended in 200 uL of absolute ethanol, centrifuged again and the supernatant removed. The ethanol rinse is performed again and the particles resuspended in a final volume of 30 uL of ethanol. An aliquot (5 mL) of the DNA-coated gold particles can be placed in the center of a flying disc (Bio-Rad Labs, 861 Ridgeview Dr, Medina, Ohio). The particles are then accelerated into the corn tissue with a PDS-1000/He (Bio-Rad Labs, 861 Ridgeview Dr., Medina, Ohio), using a helium pressure of 1000 psi, a gap distance of 0.5 cm and a flying distance of 1.0 cm.

Where *Agrobacterium* transformations were done the proceedure was accomplished essentially as described Park et al., *J. Plant Biol.* (1995), 38(4), 365–71.

Example 1

Making an Excision Reporter in Binary Vector (pBE894) to Test Germline Specificity of Promoters In order to identify male germline and common germline promoters, an excision reporter was made. In this reporter, the plant kanamycin resistance gene flanked by lox sites is inserted as a blocking fragment between a constitutive promoter and the luciferase coding region. The blocking fragment blocks the translation of luciferase by interrupting the luciferase coding sequence and such that upon cre lox excision, there is a single copy of lox site is left behind as a translational fusion with the Luciferase ORF that allows luciferase expression. The Cre gene under the control of regulated germline promoters is maintained outside the lox sites, i.e., not flanked by lox sites.

The excision reporter in binary plasmid, named pBE894, was made through the following intermediate plasmids:

pGV853 is 35S:Lox:yeast 2u:Lox:Luc (translational fusion). The coding sequence of luciferase was isolated from a 35S:luciferase gene (Promega) by PCR using primers P298 and P299 and cloned by in vivo recombination in yeast (as described in PCT WO 99/22003) to replace the GUS coding sequence in pGV796, previously digested with Eco RI and Sma I, to result in plasmid pGV853 carrying 35S: Lox:yeast 2u:Lox:Luc. The N terminus of the luciferase was translationally fused to the Lox sequence.

pGV789 is a floxed Lox 66':Avr II:Lox 71' as a translation stop in GUS gene. It was made as follows: PCR products A and B were made on pML63 carrying a 35S promoter:GUS gene using primer pairs P192, P194 and P192, P198, respectively, both were cut with Avr II, ligated, and used as template for second PCR using primers P192 and P198 to result in PCR product C, which was cut with Bgl II and Bcl I and cloned into Bgl II-Bcl I cut pML63. One skilled in the art can deduce the translation fusion from the sequences of the PCR primers used.

pGV796 is a floxed WT Lox P:Avr II:WT Lox P as a translation stop in GUS gene. It was made by PCRing the yeast trp 2 μm fragment by using PCR primers P227 P228 (that introduced wild type lox P sites at both ends) on a plasmid containing the yeast 2μ sequence and cloning it by yeast homologous recombination into Avr II cut pGV789, which has a unique Avr II sites between mutant Lox sites: 35S promoter: Lox 66'-Avr II-Lox 71' as a translation stop in GUS gene.

pGV890 is 35S:Luc blocked by a yeast 2μ fragment flanked by Lox sites. It was made by converting the Bam HI site of pGV853 to an Eco RI site. For this, pGV853 was digested with Bam HI, filled in, ligated to Eco RI linkers (New England Biolab. #1020), digested with Eco RI, and self religated.

pGV891 is 35S:Luc blocked by NPT II gene yeast (as described in PCT WO 99/22003) flanked by Lox sites. It was made by inserting the 1781 bp Avr II fragment from pGV801 containing the kanamycin resistance gene (nos:NPT II;3'nos gene) for plant transformation into the Avr II site of pGV890 in the desired orientation, i.e., same as the Luc coding sequence.

pBE892 is bar binary with floxed NPT II gene and "outside" SCP:Cre. The SCP promoter is described in Bowen, Benjamin A.; Bruce, Wesley B.; Lu, Guihua; Sims, Lynne E.; Tagliani, Laura A. Synthetic constitutive promoters for high-level expression of foreign genes in plants. U.S. (2000), 31 pp., Cont.-in-part of U.S. Ser. No. 661,601, abandoned. CODEN: USXXAM U.S. Pat. No. 6,072,050 A 20000606. It was made by cloning the Eco RI/Xba I fragment of pGV891 into Eco RI/Xba I of the bar binary pBE673 (as described in PCT WO 99/22003).

pGV895 is SCP:mCre. The Bam HI/Eco RI fragment of pHP15254 carrying bacterial Cre sequence was replaced by the Bam HI/Eco RI fragment of pHP16072 carrying the maize codon optimized Cre (described in WO 9925840) with the potato ST-LS1 intron (Leon et al. (1991) *Plant Physiol.* 95:968). The intron was inserted between the first and the second base of the $82^{nd}$ codon (for Gly).

pGV897 is SCP:mCre. It was made by introducing a Hind III site at the Eco RI site in pGV895 by ligating Hind III linkers (NEB # 1050), digesting with Hind III, and religating.

pBE894 is bar binary with floxed NPT II gene and "outside" SCP:Cre. It was made by digesting pBE892' with Xba I/Hind III and cloning in the 2159 bp Xba I/Hind III fragment from pGV897 carrying the SCP:Cre gene.

To test the vector *Agrobacterium tumefaciens* strain C58 was transformed and the resultant strain CA894 was used to transform 100 tobacco leaf discs as well known in the art. Table 1 shows that there were only 3 out of 90 discs that were alive on Kan after 4 weeks. Of these three only one showed luciferase expression by imaging. On the other hand $114/132$ (86%) discs were resistant on Bar and almost all showed luciferase expression. Thus, the excision reporter works well.

TABLE 1

Resistance in Tobacco Leaf Discs after 4 weeks

| Agrobacterium | Bar selection | Kan selection |
|---|---|---|
| None | 0/6 resistant | 0/6 resistant |
| CA894 | 114/132 resistant | 3/90 resistant |

Example 2

Identifying Promoters for Male and Common Germline Expression in *Arabidopsis thaliana*

The Xba I-Bam HI fragment of pBE894 carrying the SCP1 promoter was replaced by an Xba I-Bam HI fragment carrying one of several different developmentally-regulated promoters. These promoter regions, the PCR primers used to isolate them from genomic DNA of *Arabidopsis*, and the resultant binary plasmids are:

Promoter for Apetala 3 (AP3) gene from *Arabidopsis thaliana* Col. (pBE913).

Promoter for Bcp 1 (BCP 1) gene from *Arabidopsis thaliana* Col. (pBE914).

Promoter for Erecta (ER) gene from *Arabidopsis thaliana* Col. (pBE915).

Synthetic anther promoter (SAP) (pBE928) G9/SGB6 hybrid promoter (U.S. Pat. Nos. 5,470,359; 5,837,850)

Promoter for Pistilata (PI) gene from *Arabidopsis thaliana* Col. (pBE929).

Promoter for TA29 from tobacco (Hsu, Francis C.; Odell, Joan Tellefsen; Shen, Jennie Bih Jien. Induction of male sterility in crop plants with heterologous genes expressed from tissue-specific promoters. PCT Int. Appl. (1992), 92 pp. CODEN: PIXXD2 WO 9204454 A1, 19920319 CAN 117:209112) in pTZALG pBE855).

| Promoter | Length | Nucleotide positions (Genbank Accession #) | PCR Primers UP | LP |
|---|---|---|---|---|
| Apetala 3 (AP3) | 605 bp | 1151–1755 (U30729) | PH785 | PH786 |
| BCP 1 (BCP 1) | 579 bp | 48943–49528 (U30729) | PH783 | PH784 |
| Erecta (ER) | 1187 bp | 616–1802 (D83257) | PH788 | PH790 |
| TA29 | 1525 bp | (from plasmid pTZALG) | PH795 | PH815 |
| Pistilata (PI) | 299 bp | 2997–3296 (AB035137) | P321 | P322 |

Oligos used for PCR of promoters from *Arabidopsis* genomic DNA.

```
AP3 PCR primers
PH785:
5'-AGT CTA GAC CCG GGA TGG AAG TGA CGA TTA-3'
(SEQ ID NO:8)

PH786:
5'-GAG GAT CCC GGG TCT TCT CTC TTT GTT T-3'
(SEQ ID NO:9)

BCP1 PCR primers
PH783:
5'-TAT CTA GAC CCG GGT CTC GAT CCG ATC GAA-3'
(SEQ ID NO:10)

PH784:
5'-TTG GAT CCC GGG TTC TCT CTC TCC TTC TTA-3'
(SEQ ID NO:11)

ER PCR primers
PH788:
5'-GGT CTA GAC CCG GGA CTT TTT GAG AAA AG-3'
(SEQ ID NO:12)

PH790:
5'-ATG GAT CCC GGG TTC TCA CAC ACA GTC TTA-3'
(SEQ ID NO:13)

PI PCR primers
P321:
5'-CGT CTA GAC CCG GGA TGT TGT CTT CAA GGC-3'
(SEQ ID NO:16)

P322:
5'-ATG GAT CCC GGG TTC TCA CAC ACA GTC TTA-3'
(SEQ ID NO:17)
```

For PCR, genomic DNA (50–200 ng for each 50 μl reaction) isolated from *Arabidopsis thalania* var. Columbia, was used as the PCR reaction template unless otherwise indicated. Reaction mixtures included final concentrations of the following: 1 μM each of a 5' and 3' primer designed to amplify the desired promoter, 200 μM of each of 4 nucleotides dATP, dCTP, dGTP, dTTP; 1.25μ Amplitaq (PE Applied Biosystems, Foster City, Calif.). PCR reactions were carried out in a Perkin Elmer 9600 thermocycler (PE Applied Biosystems, Foster City, Calif.). The thermocycler was programmed as follows: a 2 min 96° C. initial denaturation step was followed by 25 cycles of 94° C., 45 sec; 55° C., 45 sec; 72° C., 90 sec, and ended with an 8 minute 72° C. final extension cycle. The desired PCR products were cloned into a PCR cloning vector pGEM-T (Promega Corp., Madison, Wis.) according to the manufacturer's protocols. After the presence of a cloned insert was established, the ends of the insert were sequenced to confirm that the desired promoter had been amplified and cloned. The cloned promoter fragments were isolated as Xba I-Bam HI fragments and cloned into binary plasmid pBE894.

TA29 promoter was isolated as a Xba I-Nco I fragment and used to replace a 35S promoter in front of the bacterial (not maize optimized) Cre ORF without intron. The chimeric gene was then cloned into a bar binary vector pBE673, described in PCT application WO 99/22003.

Binary plasmids pBE913, pBE914, pBE915, pBE928, pBE929, and pBE855 were transformed into *Agrobacterium tumefaciens* strain C58 as described in PCT application WO 99/22003.

Transformants selected on LB medium containing 100 mg/L kanamycin. Transformed bacteria were then used to transform *Arabidopsis thaliana* var. Col by the floral dip method of Clough S J, Bent A F (1998) Floral Dip: A Simplified Method for *Agrobacterium*-Mediated Transformation of *Arabidopsis thaliana*. Plant J 16:735–743. Specifically, several pots of healthy *Arabidopsis* plants were grown under long day conditions. After 4 to 6 weeks the first bolts were clipped. This encourages the proliferation of secondary bolts in 4 to 6 days. A starter culture (~200 mL of LB with antibiotics) of C58 *Agrobactium* strain carrying the gene of interest on a binary vector was grown for 2 days at 20° C. with agitation. The starter culture was used to inoculate a 2 L culture which was incubated overnight. The culture was spun down at 5,000 rpm for 10 min at RT. The cells were resuspended in 5% sucrose with 0.05% Silwet L-77 (Lehle Seeds) to an OD600 of 0.8 or higher. The above ground parts of the *Arabidopsis* plants were dipped in the Agro/sucrose solution for 2–3 seconds with agitation. The pots were laid on their side, covered with a plastic dome and placed in low light conditions for a couple of days, then uprighted and placed back into full light. After ~6 weeks the plants were allowed to dry down and the seed was harvested. Seeds were sterilized using 80% ethanol with 0.01% Triton X-100 for 10 min with agitation, 33% bleach with 0.01% Triton X-100 for 10 min with agitation followed by 5 sterile water rinses. The seeds were then suspended in 8 mL of 0.1% sterile agar and spread onto plates. The plates consist of 1×MS, 1% sucrose, 0.8% agar, 100 mg/L Timentin (Smith Kline Beecham), 10 mg/L Benomyl (DuPont) and antibiotic selection. Kanamycin sulfate (Kan) was used at 50 mg/L and glufosinate ammonium (Bar) at 20 mg/L. Resistant seedlings were removed from the plates, imaged for luciferase expression non-destructively (Tables 2–7). Lines that had no or very slight Luciferase expression (Luc +) were potted and selfed. Progeny T2 seeds of were analyzed for resistance to Kan or Bar.

The results with AP3, Bcp 1, PI, ER, and SAP show that:
(i) all these promoters were not activated in developing embryos/seeds, since there was no significant difference in transformation efficiency on Kan and Bar plates (except possibly for ER:Cre transformants, Table 5), indicating no significant excision in seeds,
(ii) all these promoters have non-specific expression in some lines, since in all seedlings resistant to Kan or Bar there was varying amounts of luciferase expression, including none, very slight (Luc +), medium (Luc ++) and high (Luc ++++). AP3 and PI constructs showed a similar distribution in Luc expression suggesting similar profile in expression specificity. AP3 and PI appear to have the most lines that show leaky expression, while Bcp 1 and SAP promoters show the least. For example, 40% of the Kan resistant seedlings showed high luc expression. In these lines AP3 is apparently serving as vegetative SAM promoter.

(iii) There was no toxicity from Cre expression in these lines, (iv) ER gave the least transformants (Table 4) and were replated (Table 5). The second plating suggest that ER:Cre may be toxic. It is not known if this toxicity, if real, is from Cre or the ER promoter.

Lines that had no or very slight Luciferase expression (Luc +) were potted and selfed. Progeny T2 seeds of were analyzed for resistance to Kan or Bar (Tables 8 and 9). These results show that AP3:Cre is a good promoter not only for vegetative SAM excision but also for floral common germline and male germline excisions. Thus, of the 17 AP3 lines analyzed at T2 stage, 9 showed 100% excision from the common (male and female) germlines, 4 showed 98% excision, 1 showed 92% excision, and one (AB07) showed male germline excision. With Bcp 1, some lines showed neither Bar or Kan resistance and may represent escapes during T1 selection. But there was one line (BK21) that showed male germline excision since Kan segregated 3:1 and Bar segregated 15:1 (two loci). When lines with common or male germline excision had more than one locus for the reporter construct, excision occurred in all loci.

TABLE 2

Analysis of transformed *Arabidopsis* seedlings (T1 progeny of plants transformed with CA913 carrying AP3:Cre) for Luciferase expression following selection on Kan or Bar.

| Selection | Luc OFF | Luc ON+ | Luc ON++ | Luc ON++++ | Total | TE (%) |
|---|---|---|---|---|---|---|
| Kan | 3 | 5 | 6 | 10 | 24 | 0.26 |
| Bar | 9 | 5 | 10 | 8 | 32 | 0.35 |
| Total | 12 | 10 | 16 | 18 | 56 | |
| % | 21 | 18 | 29 | 32 | | |

TABLE 3

Analysis of transformed *Arabidopsis* seedlings (T1 progeny of plants transformed with CA914 carrying Bcp 1:Cre) for Luciferase expression following selection on Kan or Bar.

| Selection | Luc OFF | Luc ON+ | Luc ON++ | Luc ON++++ | Total | TE (%) |
|---|---|---|---|---|---|---|
| Kan | 18 | 9 | 0 | 3 | 30 | 0.33 |
| Bar | 2 | 0 | 0 | 0 | 2 | 0.09 |
| Total | 20 | 9 | 0 | 3 | 32 | |
| % | 63 | 28 | 0 | 9 | | |

TABLE 4

Analysis of transformed *Arabidopsis* seedlings (T1 progeny of plants transformed with CA915 carrying ER:Cre) for Luciferase expression following selection on Kan or Bar.

| Selection | Luc OFF | Luc ON+ | Luc ON++ | Luc ON++++ | Total | TE (%) |
|---|---|---|---|---|---|---|
| Kan | 4 | 2 | 0 | 2 | 8 | 0.07 |
| Bar | 0 | 1 | 0 | 1 | 2 | 0.09 |
| Total | 4 | 3 | 0 | 3 | 10 | |
| % | 40 | 30 | 0 | 30 | | |

TABLE 5

Analysis of transformed *Arabidopsis* seedlings (T1 progeny of plants transformed with CA915 carrying ER:Cre) for Luciferase expression following selection on Kan or Bar.

| Selection | Luc OFF | Luc ON+ | Luc ON++ | Luc ON++++ | Total | TE (%) |
|---|---|---|---|---|---|---|
| Kan | 0 | 3 | 0 | 1 | 4 | 0.02 |
| Bar | 2 | 1 | 1 | 6 | 10 | 0.24 |
| Total | 2 | 4 | 1 | 7 | 14 | |
| % | 14 | 29 | 7 | 50 | | |

TABLE 6

Analysis of transformed *Arabidopsis* seedlings (T1 progeny of plants transformed with CA928 carrying SAP:Cre) for Luciferase expression following selection on Kan or Bar.

| Selection | Luc OFF | Luc ON+ | Luc ON++ | Luc ON++++ | Total | TE (%) |
|---|---|---|---|---|---|---|
| Kan | 20 | 6 | 2 | 1 | 29 | 0.22 |
| Bar | 5 | 5 | 0 | 0 | 10 | 0.39 |
| Total | 25 | 11 | 2 | 1 | 39 | |
| % | 64 | 28 | 5 | 3 | | |

TABLE 7

Analysis of transformed *Arabidopsis* seedlings (T1 progeny of plants transformed with CA929 carrying PI:Cre) for Luciferase expression following selection on Kan or Bar.

| Selection | Luc OFF | Luc ON+ | Luc ON++ | Luc ON++++ | Total | TE (%) |
|---|---|---|---|---|---|---|
| Kan | 22 | 23 | 34 | 17 | 96 | 1.00 |
| Bar | ND | ND | ND | ND | ND | 0.84 |
| Total | 22 | 23 | 34 | 17 | 96 | |
| % | 23 | 24 | 35 | 18 | | |

TABLE 8

Analysis of T2 progeny seeds from *Arabidopsis* transformants with CA913 (AP3:Cre) for Resistance to Bar and Kan.

| I.D. | T1 Luc | T2 Kanamycin Sensitivity | | | | T2 Bar Sensitivity | | | |
|---|---|---|---|---|---|---|---|---|---|
| | | R | S | Ratio R:S | $X^2$ P-Value (fits ratio) | R | S | Ratio R:S | $X^2$ P-Value (fits ratio) |
| AB01 | Off | 0 | 130 | 0.00 | | 156 | 0 | NA | |
| AB02 | Off | 0 | 137 | 0.00 | | 137 | 0 | NA | |
| AB03 | Off | 0 | 130 | 0.00 | | 168 | 0 | NA | |
| AB04 | Off | 0 | 142 | 0.00 | | 175 | 0 | NA | |
| AB05 | On+ | 2 | 136 | 0.01 | | 97 | 40 | 2.43 | 0.26 (for 3:1) |
| AB06 | On+ | 0 | 104 | 0.00 | | 116 | 29 | 4.00 | 0.16 (for 3:1) |
| AB07 | On+ | 77 | 59 | 1.31 | 0.12 (for 1:1) | 102 | 39 | 2.62 | 0.47 (for 3:1) |
| AB08 | Off | 0 | 137 | 0.00 | | 96 | 44 | 2.18 | 0.08 (for 3:1) |
| AB09 | On+ | 8 | 122 | 0.07 | | 72 | 49 | 1.47 | |
| AB12 | Off | 0 | 133 | 0.00 | | 133 | 0 | NA | |
| AB14 | Off | 0 | 131 | 0.00 | | 139 | 0 | NA | |
| AK02 | On+++ | 2 | 152 | 0.01 | | 115 | 49 | 2.35 | 0.15 (for 3:1) |
| AK03 | On+ | 3 | 158 | 0.02 | | 153 | 10 | NA | 0.95 (for 15:1) |
| AK05 | Off | 163 | 0 | NA | | 0 | 179 | NA | |
| AK06 | On+++ | 2 | 53 | 0.04 | | 54 | 9 | 6.00 | |
| AK08 | On+ | 2 | 181 | 0.01 | | 142 | 38 | 3.74 | 0.23 (for 3:1) |
| AK10 | On+ | 0 | 150 | 0.00 | | 114 | 31 | 3.68 | 0.31 (for 3:1) |

TABLE 9

Analysis of T2 progeny seeds from *Arabidopsis* transformants with CA914 (Bcp 1:Cre) for Resistance to Bar and Kan.

| ID | T1 Luc | T2 Kanamycin Sensitivity | | | | T2 Bar Sensitivity | | | |
|---|---|---|---|---|---|---|---|---|---|
| | | R | S | Ratio R:S | $X^2$ P-Value (fits ratio) | R | S | Ratio R:S | $X^2$ P-Value (fits ratio) |
| BB03 | On+ | 105 | 39 | 2.69 | 0.56 (for 3:1) | 84 | 13 | 6.46 | |
| BB04 | On+ | 56 | 98 | 0.57 | | 39 | 84 | 0.46 | |
| BK01 | Off | 0 | 157 | 0.00 | | 1 | 163 | 0.01 | |
| BK02 | Off | 0 | 155 | 0.00 | | 0 | 174 | 0.00 | |
| BK04 | Off | 94 | 57 | 1.65 | | 107 | 46 | 2.33 | 0.15 (for 3:1) |
| BK05 | On+ | 69 | 96 | 0.72 | | 51 | 96 | 0.53 | |
| BK06 | Off | 0 | 159 | 0.00 | | 0 | 158 | 0.00 | |
| BK07 | Off | 106 | 53 | 2.00 | | 0 | 151 | 0.00 | |
| BK08 | Off | 8 | 148 | 0.05 | | 8 | 152 | 0.05 | |
| BK09 | On+ | 66 | 84 | 0.79 | 0.14 (for 1:1) | 68 | 78 | 0.87 | 0.41 (for 1:1) |
| BK11 | On+ | 77 | 37 | 2.08 | 0.07 (for 3:1) | 118 | 25 | 4.72 | |
| BK17 | On+ | 89 | 41 | 2.17 | 0.09 (for 3:1) | 77 | 16 | 4.81 | 0.48 (for 3:1) |
| BK18 | Off | 83 | 53 | 1.57 | | 90 | 46 | 1.96 | |
| BK19 | Off | 83 | 52 | 1.60 | | 94 | 45 | 2.09 | |
| BK20 | On+ | 110 | 32 | 3.44 | 0.50 (for 3:1) | 91 | 14 | 6.50 | |
| BK21 | Off | 101 | 39 | 2.59 | 0.43 (for 3:1) | 124 | 14 | 8.86 | 0.06 (for 15:1) |
| BK22 | Off | 51 | 82 | 0.62 | | 73 | 72 | 1.01 | 0.93 (for 1:1) |
| BK23 | Off | 0 | 132 | 0.00 | | 0 | 137 | 0.00 | |
| BK24 | Off | 0 | 139 | 0.00 | | 0 | 144 | 0.00 | |

Arabidopsis transformed with the TA29:Cre (pBE855) were selected on bar and selfed. Few lines that showing single insert by 3:1 segregation in T2 were identified and these will be crossed to reporter lines to test the specificity of germline excision. Importantly these results show that there is no toxicity associated with TA29:Cre expression.

Example 3

Identifying Promoters for Marker Excision in Common Germline in Tobacco

The Xba I-Bam HI fragment of pBE894 carrying the SCP1 promoter was replaced by an Xba I-Bam HI fragment carrying one of several different developmentally-regulated promoters. These promoters and the resultant binary plasmids are:

Promoter for Heat Shock (HSP) gene from *Arabidopsis thaliana* Col. (pBE917);

Safener inducible promoter, IN 2 (pBE927) described in PCT application WO 99/22003. Promoter for Apetala 1 (AP1) gene from *Arabidopsis thaliana* Col. (pBE913).

| Promoter | Length | Nucleotide positions (Genbank Accession #) | PCR Primers UP | PCR Primers LP |
|---|---|---|---|---|
| TA29 | 1525 bp | (from plasmid pTZALG) | PH795 | PH815 |
| HSP18.2 (HSP) | 926 bp | 50050–50975 (AB006705) | PH806 | PH807 |
| Apetala 1 (AP1) | 1850 bp | 27937–29807 (AC008262) | P355 | P356 |
| Agamous (AG) | 2999 bp | 48943–49528 (AL021711) | P353 | P354 |
| Leafy (LFY) | 2287 bp | 465–2752 (M91208) | | |

Oligos used for PCR of promoters from *Arabidopsis* genomic DNA.

AP1 PCR primers
P355:
5'-CGT CTA GAC CCG GGA TGT TGT CTT CAA GGC-3'
(SEQ ID NO:20)

P356:
5'-ATG GAT CCC GGG TTC TCA CAC ACA GTC TTA-3'
(SEQ ID NO:21)

TA29 PCR primers
PH795:
5'-CCT CTA GAC CCG GGA-TTA TAT TAG GGA TTT-3'
(SEQ ID NO:14)

PH815:
5'-GCG GAT CCC GGG TAG CTA ATT TCT TTA AC-3'
(SEQ ID NO:15)

AG PCR primers
P353:

-continued
5'-CTG CCT AGG TTT CTT CTT CTT CTC GTG CTC TG-3'
(SEQ ID NO:22)

P354:
5'-GAC CCT AGG CAA TAA TTT TTT TAA AGG AAT TAA TAA GT-3'
(SEQ ID NO:23)

PCR was performed as described above and the desired PCR products were cloned into a PCR cloning vector pGEM-T (Promega Corp., Madison, Wis.) according to the manufacturer's protocols. After the presence of a cloned insert was established, the ends of the insert were sequenced to confirm that the desired promoter had been amplified and cloned. The cloned promoter fragments were isolated as Xba I- Bam HI fragments and cloned into binary plasmid pBE894.

The binary plasmids were transformed into *Agrobacterium tumefaciens* strain C58 and the resulting transformed *agrobacterium*, along with the earlier ones with AP3:Cre, Bcp1:Cre, ER:Cre used to transform *Arabidopsis*, were used to transform tobacco (*Nicotiana tabacum* var. Xanthi) by the leaf-disc method as described in PCT application WO 99/22003.

HSP:Cre in pBE894 (pBE917): Transformed leaf discs were selected on kanamycin 300. After 6 weeks, twenty four shoots were excised, placed on rooting medium containing 10 mg/L bar. The shoots were imaged for luciferase expression immediately upon transfer to rooting medium and immediately after a heat shock treatment, which consisted of placing the petri plates containing the shoots in an air incubator at 40° C. for 2 hrs for 7 d. The results of luciferase expression is shown in Table 10.

TABLE 10

| Luciferase expression in tobacco shoots before and after heat treatment. | |
|---|---|
| Shoots expressing luciferase before heat shock treatment | 8/24 (33%) |
| Shoots expressing luciferase after heats shock treatment | 22/24 (91%) |
| Shoots that showed increased luciferase upon heat shock | 19/24 (79%) |

AP3:Cre (pBE913)k: Several shoots were selected on Kanamycin and then rooted. Some of these were tested for luc expression as a reporter for excision. Some rooted plants were not expressing any luciferase and some expressed very high levels of Luciferase expression. All of these plants will be selfed and the progeny used to confirm common or male germline excisions.

Bcp 1:Cre and ER:Cre: several tobacco shoots were selected on Kan. While Bcp 1 shoots have rooted, those with ER have not. The latter may suggest that ER:Cre expression may be detrimental to root development. All rooted plants will be selfed and analyzed for excision.

What is claimed is:

1. A method of conditionally activating a transgene in a plant comprising:
   1) providing constructs comprising:
      a) a first recombinase element having the general structure P1-R1;
      b) a second recombinase element having the general structure P2-RS1-STP-RS1-R2;
      c) a third recombinase element having the general structure P3-RS2-STP-RS2-TG1; and
      d) a fourth recombinase element having the general structure P4-RS2-STP-RS2-TG2;

wherein:
   (i) P1 is a first germline promoter;
   (ii) R1 is a first recombinase coding sequence and 3' region;

(iii) RS1 is a first recombinase site responsive to a first recombinase;
(iv) P2 is a second floral common germline promoter;
(v) RS2 is a second recombinase site responsive to a second recombinase;
(vi) STP is a stop fragment;
(vii) R2 is a second recombinase coding sequence and 3' region;
(viii) TG1 is a first transgene sequence and 3' region;
(ix) TG2 is a second transgene sequence and 3' region;
(x) P3 is a third promoter which is not expressed in floral tissue and;
(xi) P4 is a fourth promoter which is not expressed in floral tissue and;
wherein P1, P2, P3 and P4 are operably linked to their down stream elements and wherein TG1 and TG2 are different trait transgenes and wherein P3 and P4 are activated in a second generation plant;
2) providing a first and second plant selected from the group consisting of:
a) a first plant comprising the first and third recombinase elements and a second plant comprising the second and fourth recombinase elements;
b) a first plant comprising the first and fourth recombinase elements and a second plant comprising the second and third recombinase elements;
3) crossing the first and second plants to produce a first generation plant wherein conditional expression of the first recombinase coding sequence (R1) under the control of the P1 promoter in the common germline of the first generation, excises the stop fragment from the second recombinase element allowing expression of the second recombinase coding sequence and 3' region (R2) under the control of P2 promoter, which recombinase, in turn, excises the stop fragments from the third and fourth recombinase elements, permitting expression of the trait gene(s) TG1 and TG2 under the control of P3 and P4 promoter, respectively, in the second generation.

2. A method for conditionally activating a transgene in somatic tissue of second generation plant comprising:
1) providing constructs comprising:
a) a first recombinase element having the general structure P1-R1;
b) a second recombinase element having the general structure P2-RS1-STP-RS1-R2;
c) a third recombinase element having the general structure P3-RS2-STP-RS2-TG;
wherein:
(i) P1 is a first germline promoter;
(ii) R1 is a first recombinase coding sequence and 3' region;
(iii) RS1 is a first recombinase site responsive to a first recombinase;
(iv) P2 is a second floral common germline promoter;
(v) RS2 is a second recombinase site responsive to a second recombinase;
(vi) STP is a stop fragment;
(vii) R2 is a second recombinase coding sequence and 3' region;
(viii) TG is a transgene sequence and 3' region which encodes a somatic trait; and
(ix) P3 is a third promoter which is active only somatic tissue:
wherein P1, P2 and P3 are operably linked to their down stream elements, and wherein the temporal expression specificity of each promoter is such that the activation of P2,
driving expression of R2, occurs concomitantly with or after P1, driving expression of R1, and the activation of P3, driving expression of TG, occurs in somatic tissues of second generation progeny plants.
2) providing a transgenic plant by a genetic cross or transformation comprising the first, second and third recombinase elements;
3) activating or inducing P1 such that the R1 recombinase coding sequence is expressed in a first generation plant, wherein expression of R1 excises the stop fragment from the second recombinase element;
4) activating P2 such that R2 is expressed, wherein expression of R2 excises the stop fragment from the third recombinase element allowing expression of the transgene in somatic tissues of the progeny plants.

3. A method for conditionally activating a transgene in a second generation plant comprising:
1) providing constructs comprising:
a) a first recombinase element having the general structure P1-R1;
b) a second recombinase element having the general structure P2-RS1-STP-RS1-R2;
c) a third recombinase element having the general structure P3-RS2-STP-RS2-TG;
wherein:
(i) P1 is a first germline promoter;
(ii) R1 is a first recombinase coding sequence and 3' region;
(iii) RS1 is a first recombinase site responsive to a first recombinase;
(iv) P2 is a second floral specific promoter;
(v) RS2 is a second recombinase site responsive to a second recombinase;
(vi) STP is a stop fragment;
(vii) R2 is a second recombinase coding sequence and 3' region;
(viii) TG is a transgene sequence and 3' region; and
(ix) P3 is a third promoter which is not expressed in floral tissue;
wherein P1, P2 and P3 are operably linked to their down stream elements, and
wherein the temporal expression specificity of each promoter is such that the activation of P2, driving expression of R2, occurs concomitantly with or after P1, driving expression of R, in the first generation common germline cells and the activation of P3, driving expression of TG, occurs in the second generation;
2) providing a transgenic plant comprising the first, second and third recombinase elements;
3) activating P1 such that the R1 recombinase coding sequence is expressed in the common germline of a first generation plant, wherein expression of R1 excises the stop fragment from the second recombinase element;
4) activating P2 such that R2 is expressed in the flower of the first generation plant, wherein expression of R2 excises the stop fragment from the third recombinase element allowing expression of the transgene in the second and all subsequent generations of plants.

4. A method for conditionally activating a transgene in somatic tissue of second generation plant comprising:
1) providing constructs comprising:
a) a first recombinase element having the general structure P1-R1;
b) a second recombinase element having the general structure P2-RS1-STP-RS1-R2;
c) a third recombinase element having the general structure P3-RS2-STP-RS2-TG;

wherein:
(i) P1 is a first germline promoter;
(ii) R1 is a first recombinase coding sequence and 3' region;
(iii) RS1 is a first recombinase site responsive to a first recombinase;
(iv) P2 is a second floral common germline promoter;
(v) RS2 is a second recombinase site responsive to a second recombinase;
(vi) STP is a stop fragment;
(vii) R2 is a second recombinase coding sequence and 3' region;
(viii) TG is a transgene sequence and 3' region which encodes a somatic trait; and
(ix) P3 is a third promoter; which is active only in somatic tissue;
wherein P1, P2 and P3 are operably linked to their down stream elements, and wherein the temporal expression specificity of each promoter is such that the activation of P2, driving expression of R2, occurs concomitantly with or after P1, driving expression of R1, and the activation of P3, driving expression of TG, occurs concomitantly with or after P2, driving expression of R2;
2) providing a transgenic plant comprising the third recombinase element;
3) transforming the transgenic plant of (2) with either the first recombinase element to generate a first plant or the second recombinase element to generate a second plant;
4) crossing the first and second plants such that expression of R1 is expressed and excises the stop fragment from the second recombinase element allowing expression of R2 under the control of P2 which, in turn, excises the stop fragment from the third recombinase element, permitting expression of the trait gene(s) under the control of P3 in the second subsequent generation(s).

5. A method for conditionally activating a transgene in a second generation plant comprising:
1) providing constructs comprising:
a) a first recombinase element having the general structure P1-R1;
b) a second recombinase element having the general structure P2-RS1-STP-RS1-R2;
c) a third recombinase element having the general structure P3-RS2-STP-RS2-TG;
wherein:
(i) P1 is a first germline promoter;
(ii) R1 is a first recombinase coding sequence and 3' region;
(iii) RS1 is a first recombinase site responsive to a first recombinase;
(iv) P2 is a second floral specific promoter,
(v) RS2 is a second recombinase site responsive to a second recombinase;
(vi) STP is a stop fragment;
(vii) R2 is a second recombinase coding sequence and 3' region;
(viii) TG is a transgene sequence and 3' region; and
(ix) P3 is a third promoter which is not expressed in floral tissue;
wherein P1, P2 and P3 are operably linked to their down stream elements, and
wherein the temporal expression specificity of each promoter is such that the activation of P2, driving expression of R2, occurs concomitantly with or after P1, driving expression of R1 in the first generation common germline cells and the activation of P3, driving expression of TG, occurs in the second generation;
2) providing a transgenic plant comprising the third recombinase element;
3) transforming the transgenic plant of (2) with either the first recombinase element to generate a first plant or the second recombinase element to generate a second plant;
4) crossing the first and second plants such that expression of R1, under the control of P1 in the common germline of the first generation, excises the stop fragment from the second recombinase element allowing expression of R2 under the control of P2 in the flower of the first generation plant which, in turn, excises the stop fragment from the third recombinase element, permitting expression of the trait gene(s) under the control of P3 in the second and subsequent generation(s).

6. A method for conditionally activating a transgene in a plant comprising:
1) providing constructs comprising:
a) a first recombinase element having the general structure P1-R1;
b) a second recombinase element having the general structure P2-RS1-STP-RS1-R2;
c) a third recombinase element having the general structure P3-RS2-STP-RS2-TG;
wherein:
(i) P1 is a first common gene promoter;
(ii) R1 is a first recombinase coding sequence and 3' region,
(iii) RS1 is a first recombinase site responsive to a first recombinase;
(iv) P2 is a second germline promoter, which is not expressed in seed
(v) RS2 is a second recombinase site responsive to a second recombinase;
(vi) STP is a stop fragment;
(vii) R2 is a second recombinase coding sequence and 3' region;
(viii) TG is a transgene sequence and 3' region, which encodes a seed trait; and
(vi) P3 is a third promoter, which is seed-specific;
wherein P1, P2 and P3 are operably linked to their down stream elements, and wherein the temporal expression specificity of each promoter is such that the activation of P2, driving expression of R2, occurs concomitantly with or after P1, driving expression of R1, and the activation of P3, driving expression of TG, occurs in progeny seed;
2) providing a transgenic plant by a genetic cross or transformation comprising the first, second and third recombinase elements;
3) activating or inducing P1 such that the R1 recombinase coding sequence is expressed in a first generation plant, wherein expression of R1 excises the stop fragment from the second recombinase element resulting in expression of the second recombinase coding sequence in floral common germline;
4) activating P2 such that R2 is expressed, wherein expression of R2 excises the stop fragment from the third recombinase element allowing expression of TG in progeny seed.

7. A method according to claim 5 where the first promoter is inducible and responsive to an inducing agent.

* * * * *

UNITED STATES PATENT AND TRADEMARK OFFICE
CERTIFICATE OF CORRECTION

PATENT NO. : 7,115,798 B1
APPLICATION NO. : 09/715294
DATED : October 3, 2006
INVENTOR(S) : Narendra S. Yadav It is certified that error appears in the above-identified patent and that said Letters Patent is hereby corrected as shown below:

Title Page,
Item (54), Column 1, Line 2, should read as follows:

-- OF TRAITS IN PLANTS USING MULTIPLE --

Column 50,
Line 45 should read as follows:

-- sion of R1, in the first generation common germline cells and --

Signed and Sealed this

Twenty-sixth Day of December, 2006

JON W. DUDAS
*Director of the United States Patent and Trademark Office*

SEQUENCE LISTING

<160> NUMBER OF SEQ ID NOS: 23

<210> SEQ ID NO 1
<211> LENGTH: 46
<212> TYPE: DNA

-continued

<213> ORGANISM: primer

<400> SEQUENCE: 1
tagcatacat tatacgaagt tattagaaga cgccaaaaac ataaag                46

<210> SEQ ID NO 2
<211> LENGTH: 44
<212> TYPE: DNA
<213> ORGANISM: primer

<400> SEQUENCE: 2
cgacgcactc cttctttagg taccgaatta cacggcgatc tttc                  44

<210> SEQ ID NO 3
<211> LENGTH: 20
<212> TYPE: DNA
<213> ORGANISM: primer

<400> SEQUENCE: 3
ccaaaagaga tctcctttgc                                             20

<210> SEQ ID NO 4
<211> LENGTH: 40
<212> TYPE: DNA
<213> ORGANISM: primer

<400> SEQUENCE: 4
gtaccctagg taccgttcgt ataatgtatg ctatacgaag                       40

<210> SEQ ID NO 5
<211> LENGTH: 20
<212> TYPE: DNA
<213> ORGANISM: primer

<400> SEQUENCE: 5
ttcacacaaa cggtgatacg                                             20

<210> SEQ ID NO 6
<211> LENGTH: 56
<212> TYPE: DNA
<213> ORGANISM: primer

<400> SEQUENCE: 6
cttcgtatag catacattat acgaagttat cctaggaaaa ggagagggcc aagagg     56

<210> SEQ ID NO 7
<211> LENGTH: 60
<212> TYPE: DNA
<213> ORGANISM: primer

<400> SEQUENCE: 7
cttcgtataa tgtatgctat acgaagttat ttacctaggc atatgatcca atatcaaagg 60

<210> SEQ ID NO 8
<211> LENGTH: 30
<212> TYPE: DNA
<213> ORGANISM: primer

<400> SEQUENCE: 8
agtctagacc cgggatggaa gtgacgatta                                  30

<210> SEQ ID NO 9
<211> LENGTH: 28

-continued

```
<212> TYPE: DNA
<213> ORGANISM: primer

<400> SEQUENCE: 9
gaggatcccg ggtcttctct ctttgttt                                    28

<210> SEQ ID NO 10
<211> LENGTH: 30
<212> TYPE: DNA
<213> ORGANISM: primer

<400> SEQUENCE: 10
tatctagacc cgggtctcga tccgatcgaa                                   30

<210> SEQ ID NO 11
<211> LENGTH: 30
<212> TYPE: DNA
<213> ORGANISM: primer

<400> SEQUENCE: 11
ttggatcccg ggttctctct ctccttctta                                   30

<210> SEQ ID NO 12
<211> LENGTH: 29
<212> TYPE: DNA
<213> ORGANISM: primer

<400> SEQUENCE: 12
ggtctagacc cgggactttt tgagaaaag                                    29

<210> SEQ ID NO 13
<211> LENGTH: 30
<212> TYPE: DNA
<213> ORGANISM: primer

<400> SEQUENCE: 13
atggatcccg ggttctcaca cacagtctta                                   30

<210> SEQ ID NO 14
<211> LENGTH: 30
<212> TYPE: DNA
<213> ORGANISM: primer

<400> SEQUENCE: 14
cctctagacc cgggattata ttagggattt                                   30

<210> SEQ ID NO 15
<211> LENGTH: 29
<212> TYPE: DNA
<213> ORGANISM: primer

<400> SEQUENCE: 15
gcggatcccg ggtagctaat ttctttaac                                    29

<210> SEQ ID NO 16
<211> LENGTH: 30
<212> TYPE: DNA
<213> ORGANISM: primer

<400> SEQUENCE: 16
cgtctagacc cgggatgttg tcttcaaggc                                   30

<210> SEQ ID NO 17
```

-continued

```
<210> SEQ ID NO 17
<211> LENGTH: 30
<212> TYPE: DNA
<213> ORGANISM: primer

<400> SEQUENCE: 17
atggatcccg ggttctcaca cacagtctta                                           30

<210> SEQ ID NO 18
<211> LENGTH: 29
<212> TYPE: DNA
<213> ORGANISM: primer

<400> SEQUENCE: 18
tttctagacc cggggaaaag agaccaagc                                            29

<210> SEQ ID NO 19
<211> LENGTH: 28
<212> TYPE: DNA
<213> ORGANISM: primer

<400> SEQUENCE: 19
ttggatcccc gggtgttcgt tgcttttc                                             28

<210> SEQ ID NO 20
<211> LENGTH: 30
<212> TYPE: DNA
<213> ORGANISM: primer

<400> SEQUENCE: 20
cgtctagacc cgggatgttg tcttcaaggc                                           30

<210> SEQ ID NO 21
<211> LENGTH: 30
<212> TYPE: DNA
<213> ORGANISM: primer

<400> SEQUENCE: 21
atggatcccg ggttctcaca cacagtctta                                           30

<210> SEQ ID NO 22
<211> LENGTH: 32
<212> TYPE: DNA
<213> ORGANISM: primer

<400> SEQUENCE: 22
ctgcctaggt ttcttcttct tctcgtgctc tg                                        32

<210> SEQ ID NO 23
<211> LENGTH: 38
<212> TYPE: DNA
<213> ORGANISM: primer

<400> SEQUENCE: 23
gaccctaggc aataatttttt ttaaaggaat taataagt                                 38
```